(12) United States Patent
Yokosawa et al.

(10) Patent No.: US 6,261,232 B1
(45) Date of Patent: Jul. 17, 2001

(54) CONTINUOUS WAVE TRANSMISSION/RECEPTION TYPE ULTRASONIC IMAGING DEVICE AND ULTRASONIC PROBE

(75) Inventors: Koichi Yokosawa, Kodaira; Ryuichi Shinomura, Kashiwa, both of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/445,890

(22) PCT Filed: Jun. 17, 1998

(86) PCT No.: PCT/JP98/02677

§ 371 Date: Mar. 30, 2000

§ 102(e) Date: Mar. 30, 2000

(87) PCT Pub. No.: WO98/57581

PCT Pub. Date: Dec. 23, 1998

(30) Foreign Application Priority Data

Jun. 8, 1997 (JP) .................................... 9-160733

(51) Int. Cl.[7] .................................................... A61B 8/00
(52) U.S. Cl. ............................................................ 600/443
(58) Field of Search .................................... 600/437, 439, 600/440–447, 453–457, 462, 381, 461, 463; 601/2, 3; 310/335, 369; 73/644

(56) References Cited

U.S. PATENT DOCUMENTS 5,655,536 * 8/1997 Takamizawa ........................ 600/447
5,967,986 * 10/1999 Cimochowski et al. ............. 600/454
6,146,329 * 11/2000 Hayakawa ........................... 600/443

* cited by examiner

Primary Examiner—Marvin M. Lateef
Assistant Examiner—Ali M. Imam
(74) Attorney, Agent, or Firm—Antonelli, Terry, Stout & Kraus, LLP

(57) ABSTRACT

A high frequency continuous wave capable of achieving sufficient lateral resolution is produced by a wave transmitting device (20) to constitute a transmitted ultrasonic wave. A frequency of the continuous wave is alternated in a rectangular wave manner by a frequency modulator (15) so as to be frequency-modulated. An alternating time period of the frequency modulation is set to such time two times longer than such delay time which is defined from a time instant when a signal voltage is applied to a piezoelectric transducer element (1) up to another time instant when an ultrasonic wave originated from the piezoelectric transducer is reflected from a focal point 5 and then is reached to the piezoelectric transducer element. In a delay circuit (35), a delay equal to the delay time is applied to the transmitted ultrasonic wave so as to be used as a reference signal. A mixture signal produced by mixing the transmitted ultrasonic wave with the received ultrasonic wave is lock-in-detected (55), so that a reflection signal reflected from the checking object is selectively detected. As a result of increasing a total wave number of transmitted/received waves per unit time, since the continuous wave ultrasonic wave is irradiated onto the checking subject, for instance, in the case that living body tissue is imaged with high resolution at a cell level, S/N is improved.

26 Claims, 12 Drawing Sheets

CONTINUOUS WAVE TRANSMISSION/RECEPTION TYPE ULTRASONIC IMAGING DEVICE AND ULTRASONIC PROBE

TECHNICAL FIELD

The present invention is related to a continuous wave transmission/reception type ultrasonic imaging apparatus for measuring very fine tissue nature of organ interiors within a body, organ surfaces, and body surfaces in real time, and also is related to an ultrasonic probe.

BACKGROUND ART

A living body (biological body) investing method (biopsy) is known to diagnose morbi (diseases) occurred in organs. In the biopsy, while organs located inside a body cavity are imaged by an ultrasonic imaging apparatus, a piercing needle is pierced up to a morbus (disease) portion so as to pickup biological body tissue of a region of interest (ROI) inside the piercing needle. The picked biological body tissue is discriminated to judge a disease name. However, after the biological body tissue has been extracted, or removed outside the living body, this extracted biological body tissue is fixed, cut in a thinner size, and stained so as to be investigated in the biopsy. As a consequence, this biopsy owns a problem that several weeks are necessarily required to diagnose such an extracted biological body tissue, another problem that the extracted biological body tissue is changed from a living state within the living body, and another problem that a tree-dimensional image can be hardly acquired.

To solve the above-described problems, the following needle-shaped ultrasonic probe has been proposed. That is, while the ultrasonic wave converter is mounted on the piercing needle, this piercing needle is directly pierced into the region of interest so as to measure the tissue characteristic stage of the region of interest, or to image living body tissue located around the region of interest. As the conventional needle-shaped ultrasonic probe, for instance, there are "PROBE MADE BY THAT CONCAVE IS FORMED IN NEEDLE, AND ULTRASONIC WAVE CONVERTER IS PROVIDED ON WALL SURFACE OF CONCAVE" (Japanese Patent Publication No. Hei-4-78299: first prior art), and "PROBE MADE BY THAT INNER NEEDLE OF PIERCING NEEDLE IS REPLACEABLE WITH ULTRASONIC WAVE CONVERTER" (Japanese Patent Publication No. Hei-6-125: second prior art). In the ultrasonic probes of the first and second prior art, acoustic characteristic such an sound velocities and reflectivities of living body tissue located around regions of interest are measured by employing ultrasonic waves, or ultrasound.

As another example of such an ultrasonic probe for imaging biological body tissue located around this ultrasonic probe based upon a acoustic characteristic (sound velocity and reflectivity) of this biological body tissue, the following prior art is known. For instance, there are "PROBE FOR SCANNING ULTRASONIC WAVE CONVERTER, MADE BY THAT WHILE OPENING PORTION IS FORMED IN A PORTION OF OUTER NEEDLE, ULTRASONIC WAVE CONVERTER MOUNTED ON SIDE SURFACE OF INNER NEEDLE IS EXPOSED TO OPENING UNIT" (Japanese Patent Publication No. Hei-5-9097: third prior art), and also "PROBE FOR EXPOSING INNER NEEDLE ON WHICH ULTRASONIC WAVE CONVERTER IS MOUNTED FROM TIP PORTION OF OUTER NEEDLE" ("ULTRASONIC IMAGING" magazine, volume 15, pages 1–13, 1993): fourth prior art).

The third prior art and the fourth prior art correspond to the arrangements for acquiring the images of the plane perpendicular to the axis of the needle, or the plane involving the axis of the needle, a so-called "B-mode image". The higher the frequency of the ultrasonic wave employed in the ultrasonic imaging operation is increased, the shallower the penetration depth by the ultrasonic wave becomes due to absorptions by the living body tissue. As a result, since the visual field is narrowed, the frequencies of the ultrasonic waves used in the imaging method capable of acquiring the B-mode image are selected to be lower than, or equal to approximately 100 MHz. To avoid such a problem that the penetration depth of the ultrasonic wave becomes shallow and thus the visual field is narrowed, which is caused by the condition that the ultrasonic wave converter with high resolution, operable in higher frequencies than, or equal to 100 MHz, another conventional method (Japanese Patent Application Laid-open No. Hei-8-154936; fifth prior art) has been proposed. That is, this imaging method acquires the image of the cylindrical plane (curved plane) around the needle, a so-called "cylindrical type C-mode" image.

In the ultrasonic probes of the fourth prior art and the fifth prior art, the ultrasonic wave converters equipped with the acoustic lenses are provided inside the needles in order to improve the lateral resolution. The ultrasonic waves which are produced from the piezoelectric transducer elements energized by the transmitted ultrasonic wave voltage are propagated within the acoustic lens materials to be converged. Then, the converged ultrasonic waves are reflected at the positions in the vicinity of the focal points of the acoustic lenses, so that the reflection signals are produced. The reflection signals are propagated through the opposite path to the piezoelectric transducer element to be converted into the voltages.

In general, when such an arrangement for improving lateral resolution with employment of an acoustic lens is used, a transmitted ultrasonic wave is a pulse wave so as to secure resolution along a depth direction (namely, radial direction while setting axis of needle as a center). In the case that such a pulsatory ultrasonic wave is transmitted, a distribution occurs in delay time defined until a reflection signal reaches a piezoelectric transducer element, depending upon a position of a reflector for reflecting a transmitted ultrasonic wave signal. In other words, the delay time may give positional information along the depth direction.

In the fourth prior art, while using such a fact that the delay time may give the positional information along the depth direction, the image along the depth direction is acquired. Also, in the fifth prior art, the imaging plane is set by time-gating the received ultrasonic waves on the wave reception side. In other words, while the signals having certain constant delay time are detected, the cylindrical plane is imaged, and this cylindrical plane is separated from the axis of the needle by a constant distance. In any cases, while the delay time and the time approximated to this delay time are time-gated so as to selectively detect the reflection signal reflected from the interiors of the living body tissue. The time gating operation given to the received ultrasonic wave signals may separate the transmitted ultrasonic wave signal from the received ultrasonic wave signal in the temporal manner, and therefore may avoid entering of the transmitted ultrasonic waves into the wave receiving device.

The method for transmitting the ultrasonic wave by using the burst wave is known in ultrasonic micro-scopes. In the case that the ultrasonic wave converter cannot be sufficiently energized by the pulse wave, since this ultrasonic wave converter is energized by using such a burst wave, S/N can be improved. Also, another method is known. That is, the multiple reflections within the acoustic lens material will interfere with the reflection signals by using the burst signal so as to improve the depth resolution.

The duration time of the burst wave used in the method for improving either S/N or the depth resolution is made shorter than the delay time defined between the ultrasonic wave transmission and he arrivals of the reflection signals (in most case, sufficiently shorter than delay time). Similar to the method with employment of the pulse wave, the time gate is provided on the reception side of the burst ultrasonic wave so as to separate the transmitted ultrasonic wave from the received ultrasonic wave.

To discriminate tissue from a characteristic state of biological body time, lateral resolution with a cell level is required. As is well known in this field, when a frequency of an ultrasonic wave is increased, a wavelength of the ultrasonic wave is shortened, so that lateral resolution may be increased. However, absorptions of ultrasonic waves by the living body tissue are also increased. Since the absorptions of the ultrasonic waves are increased, the strengths of the reflection signals are considerably decreased. This may cause such a problem that S/N would be lowered.

FIG. 21 represents attenuations of amplitudes, which are caused by absorptions by kidney and liver. Apparently, the absorptions are considerably emphasized in a frequency range higher than, or equal to 100 MHz.

It should be understood that the graphic representation shown in FIG. 21 is made by considering FIG. 4.10 (see page 176) in section 4 of publication entitled "Physical principles of medical ultrasonics".

The structures of the needle-shaped ultrasonic probes according to the first prior art and the second prior art own such a problem that since only one measuring point is obtained, sufficiently much information required for the diagnoses cannot be obtained. Also, in the arrangements for acquiring the B-mode image according to the third prior art and the fourth prior art, since the absorptions by the high frequency ultrasonic waves higher than, or equal to 100 MHz are increased, it is practically difficult to employ such high frequency ultrasonic waves higher than, or equal to 100 MHz. There is a problem that the resolution at the cell level could not be realized.

In the method for imaging the cylindrical plane around the needle by the C-mode image explained in the fifth prior art, it is possible to use such ultrasonic waves having the frequencies selected between 100 MHz and 200 MHz, so that the resultant resolution may be increased up to approximately 10 $\mu$m. The resolution with on the order of 10 $\mu$m is substantially equal to a dimension of a cell. In order to observe a characteristic state of biological higher resolution, it is desirable to use ultrasonic waves having frequencies nearly equal to 400 MHz. When the ultrasonic waves having the higher frequencies, i.e., on the order of 400 MHz are employed, since absorptions of these ultrasonic waves by the biological body tissue are increased, the strengths of the transmission signals need be largely increased at degrees higher than the degrees capable of compensating for the absorptions of the ultrasonic waves, and the S/N must be maintained.

DISCLOSURE OF INVENTION

Now, the following definition is made in the specification of the present invention. That is, an expression "delay time" is defined by "a time difference between a time instant when a piezoelectric transducer element is energized by a transmitted ultrasonic wave voltage, and another time instant when an ultrasonic wave produced by energizing the piezoelectric transducer element is propagated to a focal distance of an acoustic lens and is reflected, and the reflected ultrasonic wave is again propagated to the piezoelectric transducer element to be again converted into a voltage".

An object of the present invention is to provide a continuous wave transmission/reception type ultrasonic imaging apparatus and an ultrasonic probe, capable of extracting very fine characteristic states of tissue such as organ interiors within a living body, surfaces of organs, and surfaces of a biological body in real time so as to readily perform a diagnosis, while both a strength of a reception signal and lateral resolution are improved. A novel feature of the present invention may become apparent from the descriptions of the present specification and the accompanying drawings.

Next, a description will now be simply made of a typical arrangement of the present invention.

To improve both a reception signal strength and lateral resolution, it is so arranged that an ultrasonic wave made of a continuous wave is transmitted to a checking object. Generally speaking, when noise "N" is constant, S/N is direct proportion to a root-mean-square of a total wave number of transmitted/received ultrasonic waves. In other words, the larger a total wave number of these transmitted/received ultrasonic waves is increased, the higher the strength of the reception signal is increased. Such a technical point of the present invention is different from that of the previously explained prior art (in particular, method for employing burst wave). That is to say, duration time of a transmitted ultrasonic wave made of a continuous wave is made sufficiently longer than such delay time which is defined as follows: A transmitted ultrasonic wave is reflected from a checking object, and then the reflected ultrasonic wave is reached to a piezoelectric transducer element.

In the case that an ultrasonic wave made of a continuous wave is employed, the duration time of which is sufficiently long, a received ultrasonic signal cannot be time-gated. Therefore, there is such a problem that a transmitted ultrasonic wave signal whose magnitude is 100 to 1,000 times larger than that of a received ultrasonic wave signal will be entered into a wave receiving device. To solve such a problem that the transmitted ultrasonic signal is entered into the wave receiving device, a frequency of a transmitted ultrasonic wave is frequency-modulated to continuously make the frequency of the transmitted ultrasonic wave different from the frequency of the received ultrasonic wave. As a result, the transmitted ultrasonic wave signal is separated from the received ultrasonic wave signal. The separation between the transmitted/received ultrasonic waves by way of the frequency, and also the modulation of the transmitted ultrasonic wave frequency will be discussed more in detail.

More, specifically, the present invention will now be considered as to such a case that the invention idea of the present invention is applied to a needle-shaped ultrasonic probe for performing a cylindrical plane C-mode imaging operation which is similar to the fifth prior art. As previously explained, in the prior art, the received ultrasonic wave signal is time-gated to thereby set the imaging plane. In other words, it is conceivable that a constant focal depth is located in the vicinity of the acoustic lens, and the reflection signals are mainly produced within the focal depth of the acoustic lens. Although the degree of freedom in setting of the focal depth is deteriorated, as compared with the conventional time-gate method, the imaging plane can be determined based upon the shape of the acoustic lens.

In the prior art with employment of the pulse wave, the resolution along the depth direction depends upon the temporal resolution of the pulse wave. In other words, the frequency range of the pulse wave must be made wide as being permitted as possible. Since the frequency range is widened, color aberration occurs at the focal point of the acoustic lens, which may cause the lateral resolution to be deteriorated. In accordance with the present invention, since the continuous wave is employed as the transmitted ultrasonic wave, the frequency range is narrowed. The color aberration is reduced and the lateral resolution is improved. Moreover, the frequency range of the wave receiving device can be made narrow, and the white noise can be reduced. Since the white noise is reduced, the resultant S/N may also be improved.

In the conventional technique, when the time gate is set within the range of the focal depth, the images of a plurality of imaging planes located in the different depths can be acquired. In principle, in accordance with the present invention, the imaging plane is determined, depending upon the acoustic lens.

In accordance with the present invention, the imaging plane is determined by the acoustic lens. In the case that a plurality of imaging planes having different depths are required for the diagnostic purpose, namely in such a case that although not so perfect 3-dimensional image is required, a three-dimensional image with 2.5-dimension is required which is acquired from a plurality of imaging planes, a plurality of ultrasonic wave converters having such acoustic lenses whose focal point positions are different from each other are provided within a single ultrasonic probe. Then, images of a plurality of imaging planes having the different depths are obtained by employing a plurality of ultrasonic wave converters. In this arrangement, in order to prevent mutual interference occurred among these ultrasonic wave converters, all of timing with respect to the transmitted/received ultrasonic waves from the respective ultrasonic wave converters are set to be different from each other. Thus, it is possible to draw a three-dimensional structure of biological body tissue.

Also, in an arrangement of the present invention, while the frequency of the transmitted ultrasonic wave is frequency-modulated, the transmitted ultrasonic wave is alternated between at least more than 2 frequencies, for example, a frequency "f1" and another frequency "f2" by way of the frequency modulation of the transmitted ultrasonic wave. When the transmitted ultrasonic wave is alternated between the frequencies f1 and f2 so as to acquire the received ultrasonic wave signal, the signal produced by the frequency f1 and the signal produced by the frequency f2 are separately acquired by different data acquiring apparatuses, so that the images (f1-image and f2-image) having the different frequencies can be separately obtained. In general, an acoustic characteristic of living body tissue may depend upon a frequency. For instance, in such tissue which largely absorbs ultrasonic waves, there is a large difference in signal strengths between the image obtained in the low frequency and the image obtained in the high frequency. As a result, it is possible to obtain an ultrasonic wave absorbing distribution of biological body tissue from a difference image between the f1-image and the f2-image. As to the difference image, there is a clear difference in the signal strengths, as compared with the ultrasonic wave absorbing distribution obtained by a single frequency. There is such an effect that the tissue characteristic states with higher orders can be drawn to achieve an easy diagnose.

The present invention will now be summarized as follows: While a high frequency continuous wave capable of obtaining sufficient lateral resolution is employed as the transmitted ultrasonic wave, the frequency of the continuous wave is alternated in a rectangular-shaped manner, and is frequency-modulated. The alternating time period of the frequency modulation is set to be two times (2t) longer than the delay time. This delay time is defined between the time instant when the signal voltage is applied to the piezoelectric transducer element, and the time instant when the ultrasonic wave produced from the piezoelectric transducer element is reflected from the focal point (checking subject), and then the reflected ultrasonic is reached to the piezoelectric transducer element. Furthermore, while the delay equal to the delay time is applied to the transmitted ultrasonic wave so as to produce the reference signal, the signal produced by mixing the transmitted ultrasonic wave with the received ultrasonic wave is lock-in-detected, so that the reflection signal derived from the object under examination is selectively detected. As a result of increasing of a total wave number of the transmitted/received ultrasonic waves per unit time, since the ultrasonic wave made of the continuous wave is irradiated to the object under examination, the resultant S/N can be improved in such a case that the biological body tissue is imaged with high resolution in the cell level.

BEST MODE FOR CARRYING OUT THE INVENTION

Figure 1:
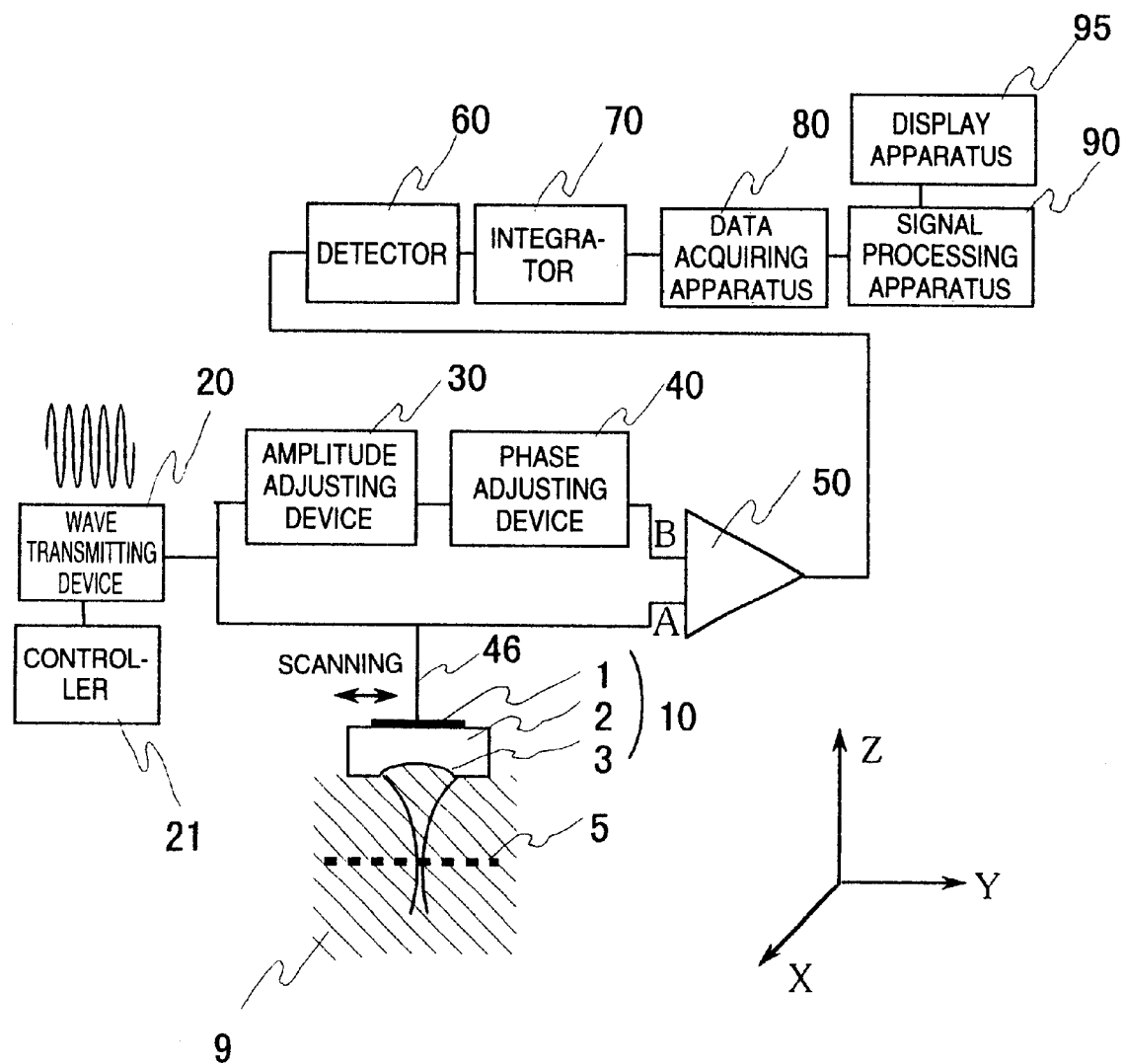
FIG. 1 is a block diagram for indicating an arrangement of an apparatus according to a first embodiment of the present invention.

Referring now to drawings, an embodiment of the present invention will be explained in detail. It should be noted that the same reference numerals shown in all drawings used to explain the respective embodiments will be employed as those for indicating the units having the same functions, and explanations thereof are omitted.

(First Embodiment)

FIG. 1 is a block diagram for schematically indicating an arrangement of a continuous wave transmission/reception type ultrasonic imaging apparatus according to a first embodiment of the present invention.

Figure 2:
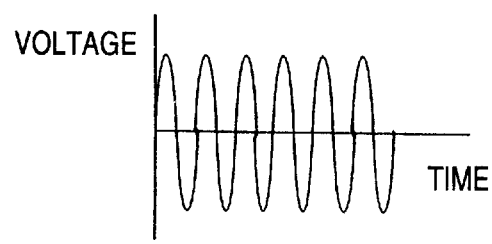
FIG. 2 is a diagram for showing a temporal change of a transmitted ultrasonic wave voltage in the first embodiment of the present invention.

FIG. 2 is a diagram for showing a temporal change of a transmitted ultrasonic wave voltage in the first embodiment of the present invention, and the transmitted ultrasonic wave frequency is a sine wave whose frequency is constant (f0).

Figure 3:
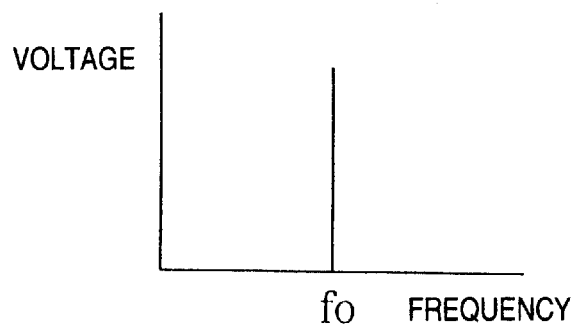
FIG. 3 is a diagram for representing a frequency characteristic of a mixture signal produced by mixing a transmitted ultrasonic wave with a received ultrasonic wave in the first embodiment of the present invention.

FIG. 3 is a diagram for representing a frequency characteristic of a mixture signal produced by mixing a transmitted ultrasonic wave with a received ultrasonic wave in the first embodiment of the present invention.

In FIG. 1, an acoustic lens 3 of an ultrasonic wave converter 10 is directly made in contact with an object under examination, for example, biological body (living body) tissue 9 of invivo. A piezoelectric transducer element 1 transduces a continuous sine wave oscillated from a wave transmitting device 20 into an ultrasonic wave. A controller 21 controls the wave transmitting device 20 in such a manner that duration time required to transmit an ultrasonic wave by an ultrasonic wave converter 10 becomes longer than delay becomes longer than delay time. The ultrasonic waves propagated through an acoustic lens material 2 are converted by the acoustic lens 3 to be focused within the object under examination, and also are reflected on the propagation path. The reflected ultrasonic wave is again converted into a voltage by the piezoelectric transducer element 1, and then this voltage is entered into a differential amplifier 50 corresponding to a wave receiving device. Reference numeral 46 indicates a signal line used to transmit/receive an ultrasonic wave.

In the arrangement shown in FIG. 1, a focal point of the acoustic lens 3 owns such a focal depth which is defined by a strength of an ultrasonic wave, namely a half-width of sound pressure. It may be considered that a reflection wave is mainly originated from a range of the focal depth. As a consequence, since the ultrasonic wave transducer 10 is mechanically scanned along an x direction and a y direction within a plane perpendicular to a wave transmitting/receiving direction (namely, upper/lower direction, or z direction in FIG. 1) of an ultrasonic wave, a distribution image of ultrasonic wave reflectivities of a plane 5 can be obtained. This plane 5 is defined by a trail (locus) of the focal point of the acoustic lens 3 in connection with the scanning operation of the ultrasonic wave transducer 10.

In the apparatus of FIG. 1, the ultrasonic wave transmitted from the wave transmitting device 20 and the received ultrasonic wave are entered into the differential amplifier 50 corresponding to the wave receiving device at the same time. In the first embodiment, as shown in FIG. 3, while the frequency of the transmitted ultrasonic wave is always identical to the frequency of the received ultrasonic wave, generally speaking, the magnitude of the transmitted ultrasonic wave is approximately 100 to 1000 times larger than the magnitude of the received ultrasonic wave. As a result, the transmitted ultrasonic wave may cause the received ultrasonic wave to be troubled. In the arrangement shown in FIG. 1, since the frequency of the transmitted ultrasonic wave is equal to the frequency of the received ultrasonic wave, the received ultrasonic wave is extracted as follows. Prior to a measurement of an ultrasonic reflectivity of an object under examination, an amplitude adjusting device 30 and a phase adjusting device 40 are adjusted in such a manner that an output of a differential amplifier 50 corresponding to a wave receiving device is made equal to zero by employing a reference sample such as a physiological salt solution. In other words, while such a signal equivalent to a transmitted ultrasonic wave signal which is entered into a terminal "A" of the differential amplifier 50 is inputted to another terminal "B" of the differential amplifier 50, the ultrasonic reflectivity of the object under examination is measured. As a result, the reflection signals reflected from the interior of the biological body can be mainly detected as the output derived from the differential amplifier 50. In the arrangement shown in FIG. 1, the wave receiving device detects a difference between a reference signal and the output signal of the ultrasonic wave converter. This reference signal is produced by adjusting an amplitude and a phase of a transmitted ultrasonic wave signal.

While the ultrasonic wave converter 10 is mechanically scanned along both the x direction and the y direction and this scanning operation is stopped at each of the scanning positions only for a necessary time period so as to transmit/receive the ultrasonic waves, the signal outputted from the differential amplifier 50 functioning as the wave receiving device, which corresponds to the result of the ultrasonic wave transmission/reception, is detected by a detector 60.

Thereafter, the detected signals are integrated by an integrator 70, so that a sufficient S/N can be obtained. Also, since the frequency range of the differential amplifier 50 functioning as the wave receiving device may be sufficiently narrowed in connection with the frequency of the transmitted ultrasonic wave, white noise can be reduced. Among such ultrasonic waves reflected from the focal point of the acoustic lens, it is possible to receive all of the signals produced from ultrasonic waves which are reflected multiple times inside the acoustic lens material 2 and are delayed. Accordingly, the S/N can be further improved. The signals outputted from the integrator 70 are acquired by a data acquiring apparatus 80, and then the acquired signal is processed by a signal processing apparatus 90. The result of this signal process operation is displayed on a display apparatus 95.

(Second Embodiment)

Although the first embodiment has a merit that the arrangement is made simple, the differential amplifier 50 requires the sufficient dynamic range. Subsequently, a second embodiment (FIG. 4) will now be explained as follows, in which a frequency of a transmitted ultrasonic wave and a frequency of a received ultrasonic wave are made different from each other, and the transmitted ultrasonic wave is separated from the received ultrasonic wave based upon a frequency to secure a dynamic range. It should be noted that since an arrangement for setting an imaging plane by a focus point area, and also an effect capable of reducing white noise by sufficiently narrowing a frequency range of a received ultrasonic wave according to the second embodiment are similar to those of the first embodiment, the previously-explained items in the first embodiment (FIG. 1) are omitted, and then a method for separating a transmitted ultrasonic wave from a received ultrasonic wave will be discussed later in the below-mentioned description.

Figure 5:
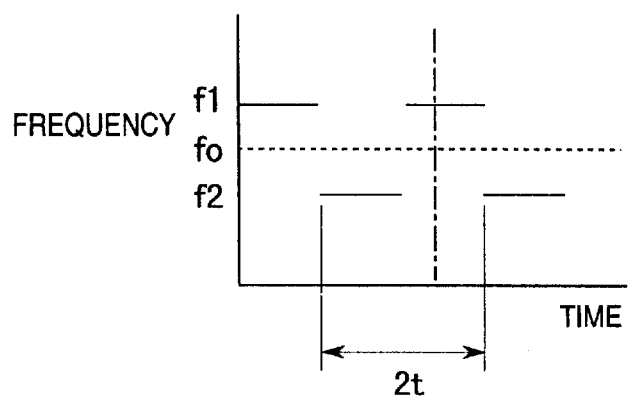
FIG. 5 is a diagram for showing a temporal change of a transmitted ultrasonic wave frequency in the second embodiment of the present invention.
Figure 4:
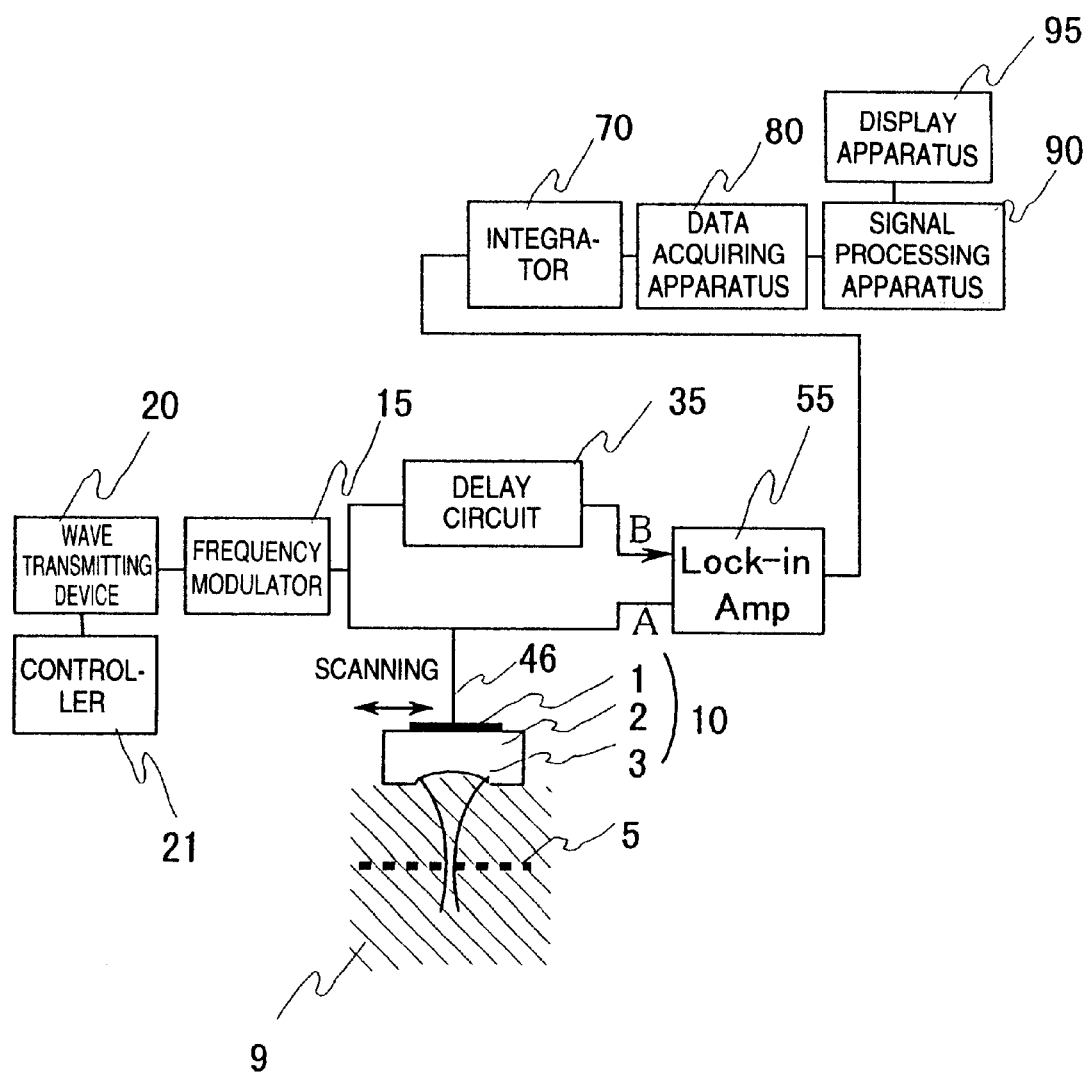
FIG. 4 is a block diagram for indicating an arrangement of an apparatus according to a second embodiment of the present invention.
Figure 6:
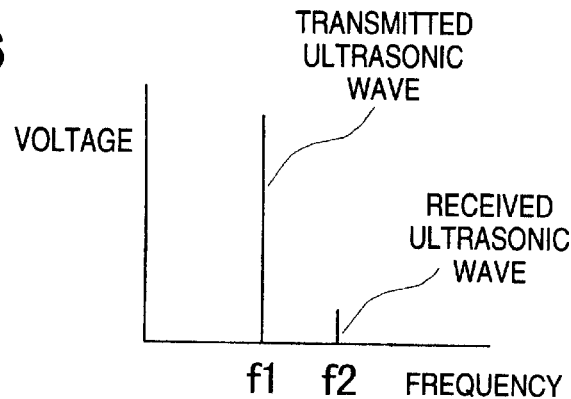
FIG. 6 is a diagram for representing a frequency characteristic of a mixture signal produced by mixing a transmitted ultrasonic wave with a received ultrasonic wave in the time indicated by a dot/dash line of FIG. 5.
Figure 7:
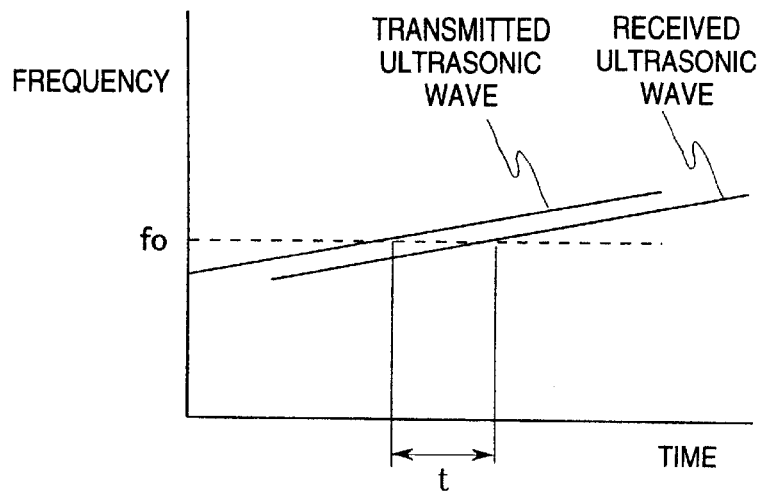
FIG. 7 and FIG. 8 are diagram for showing temporal changes of a transmitted ultrasonic wave frequency and a received ultrasonic wave frequency in such an example that the continuous wave according to the second embodiment of the present invention is transmitted.
Figure 8:
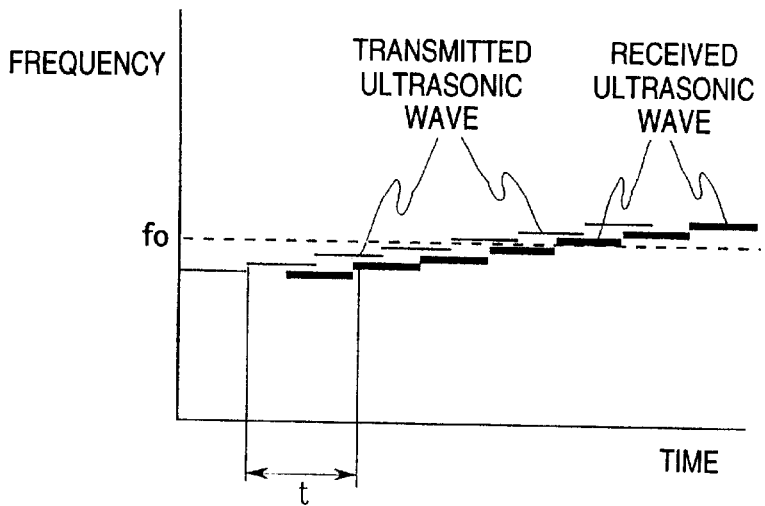

FIG. 4 is a block diagram for schematically showing an arrangement of a continuous wave transmission/reception type ultrasonic imaging apparatus according to a second embodiment. Reference numeral 15 shows a frequency modulator, reference numeral 35 indicates a delay circuit for applying delay time "t" to a transmitted ultrasonic wave to produce a reference signal, and also reference numeral 55 represents a lock-in-amplifier (Lock-in-Amp) corresponding to an ultrasonic wave receiver. Instead of controlling the wave transmitting device 20 by the controller 21, the frequency modulator 15 is controlled by the controller 21 in such a manner that the duration time of the transmitted ultrasonic wave by the ultrasonic wave converter 10 is prolonged. Alternatively, the frequency modulator 15 may be controlled in such a manner that the duration time of the transmitted ultrasonic wave by the ultrasonic wave converter 10 becomes longer than the delay time. Any of FIG. 5, FIG. 6, FIG. 7, and FIG. 8 are explanatory diagrams for explaining that the transmitted ultrasonic wave is frequency-modulated, and the ultrasonic wave transmission/reception separation is carried out by the frequency. FIG. 5 is a diagram for showing a temporal change of a transmitted ultrasonic wave frequency in the second embodiment of the present invention. FIG. 6 is a diagram for representing a frequency characteristic of a mixture signal produced by mixing a transmitted ultrasonic wave and a received ultrasonic wave in the time indicated by a dot/dash line of FIG. 5. FIG. 7 and FIG. 8 are diagram for showing temporal changes of a transmitted ultrasonic wave frequency and a received ultrasonic wave frequency in such an example that the continuous wave according to the second embodiment of the present invention is transmitted.

In the second embodiment, the frequency modulation is carried out to transmit the ultrasonic wave in such a manner that such a frequency is given and is alternated in a rectangular wave manner between two frequencies "f1" and "f2" which sandwich a resonant frequency C center frequency) "f0" of the ultrasonic wave converter. In this second embodiment, assuming now that a time difference (delay time) between a time instant when a signal voltage is applied to the piezoelectric transducer element 1 and another time instant is defined as "t", the alternate period of the frequency modulation is set to "2t". The last-mentioned time instant is defined by such that the ultrasonic wave is reflected from the focal point and thereafter, is reached to the piezoelectric transducer element 1.

In other words, the frequencies f1 and f2 are alternated while being held by the time "t" (delay time), respectively. In the second embodiment, when the frequency of the transmitted ultrasonic wave is "f1", the frequency of the received ultrasonic wave is always "f2". Conversely, when the frequency of the transmitted ultrasonic wave is "f2", the frequency of the received ultrasonic wave is always "f1". As indicated in FIG. 6, since the frequencies of the transmitted/received ultrasonic waves are always different from each other, while the delay time "t" is applied to the transmitted ultrasonic wave to produce the reference signal, the signal in which the transmitted ultrasonic wave is mixed with the received ultrasonic wave is lock-in-detected, so that only the reflection signal can be mainly detected.

For instance, when the frequency "f0" is 400 MHz, assuming now that the difference between the frequencies f1 and f2 is on the order of 1 MHz, these frequencies f1 and f2 can be sufficiently separated from each other. It may be considered that then is substantially no difference between the image made from the frequency f1 and the image made from the frequency f2. The frequency modulation of the transmitted ultrasonic wave may be varied in a sinusoidal periodic manner, not in the rectangular manner. Since the frequency of the transmitted ultrasonic wave is located close to the frequency of the received ultrasonic wave when the frequencies are alternated, there is a problem that the separation between the transmitted ultrasonic wave and the received ultrasonic wave is deteriorated.

In FIG. 5 and FIG. 6, the simplest example is exemplified. In a general format, assuming now that either an alternating period of a frequency of a transmitted ultrasonic wave, or a periodic change period of a transmitted ultrasonic wave is equal to "T", and also delay time is equal to "t", it is so that to T=2t/(2n−1) (symbol "n" being a natural number). Furthermore, the wave receiving device refers to such a transmitted ultrasonic wave signal which is delayed by (2n−1)T/2, or time equal to "t(delay time)", so that the completely same effect as that of the first embodiment can be achieved.

FIG. 7 is a graphic representation for showing another example of the frequency modulation of the transmitted ultrasonic wave, namely such a condition that a frequency of a mixture signal obtained by mixing a transmitted ultrasonic wave with a received ultrasonic wave is changed in a temporal manner. Even in such a frequency modulation case that the frequency of the transmitted ultrasonic wave is continuously varied (see FIG. 7), while the delay time "t" is applied to the transmitted ultrasonic wave to produce a reference signal, the mixture signal made of the transmitted ultrasonic wave and the received ultrasonic wave is lock-in-detected, so that only the reflection signals can be mainly detected. It should be understood that the temporal change in the frequencies of the reference signal is identical to the temporal change in the frequency of the received ultrasonic wave shown in FIG. 7.

The frequency modulation of the transmitted ultrasonic wave indicated in FIG. 7 owns such an advantage that the time period of the frequency modulation of the transmitted ultrasonic wave need not be set to be equal to "t" (delay time), but the frequency of the transmitted ultrasonic wave can be readily set. The above-explained frequency modulation example of the transmitted ultrasonic wave shown in FIG. 7 may be modified. That is, as represented in FIG. 8, while a frequency is changed in a step shape, the transmitted ultrasonic wave may be frequency-modulated. The frequency modulation example of the transmitted ultrasonic wave indicated in FIG. 8 has a merit that the lock-in-detection can be easily carried out. In the frequency modulation example of the ultrasonic wave shown in FIG. 8, both the duration time of the frequency of the transmitted ultrasonic wave and the duration time of the frequency of the received ultrasonic wave must be made shorter than the delay time "t" in order to avoid such a condition that the frequency of the transmitted ultrasonic wave becomes coincident with the frequency of the received ultrasonic wave. It should also be noted that the temporal change in the frequencies of the reference signal obtained by giving the delay time "t" to the transmitted ultrasonic wave is identical to the temporal change of the received ultrasonic wave shown in FIG. 8.

(Third Embodiment)

Figure 9:
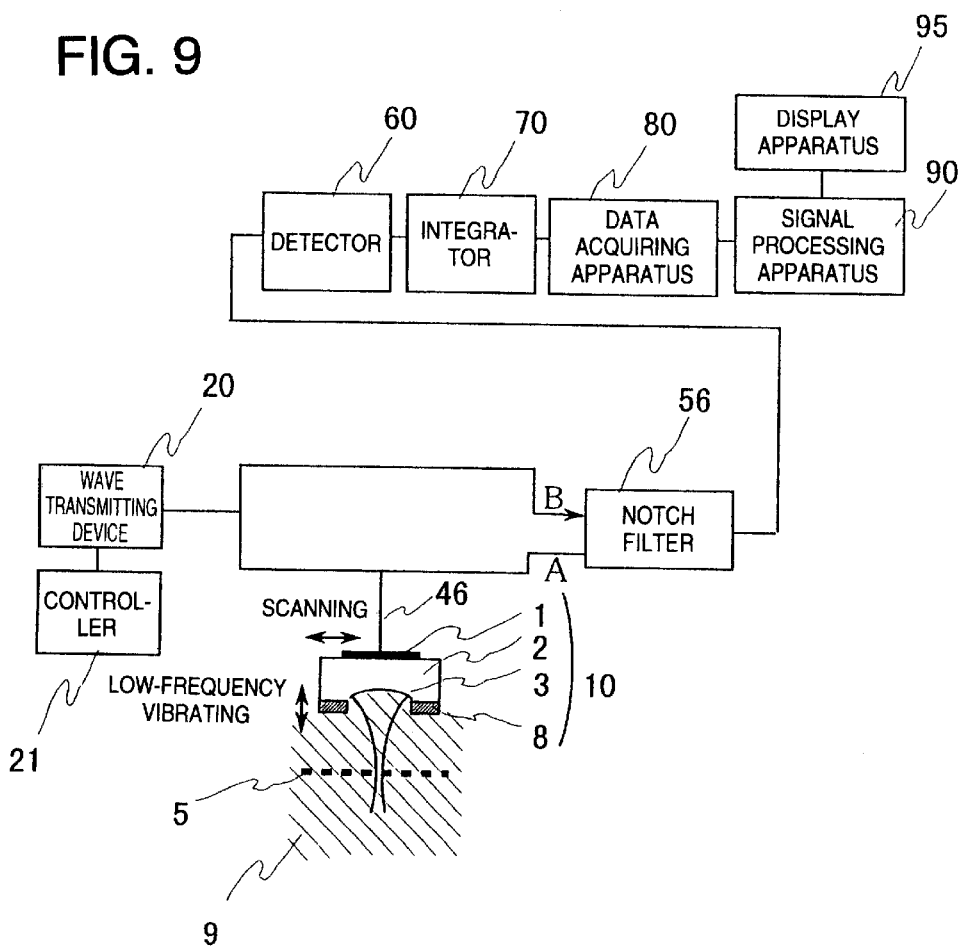
FIG. 9 is a block diagram for indicating an arrangement of an apparatus according to a third embodiment of the present invention.

FIG. 9 is a block diagram for schematically showing an arrangement of a continuous wave transmission/reception type ultrasonic imaging apparatus according to a third embodiment. Reference numeral 8 is a piezoelectric transducer element having a low resonant frequency, and reference numeral 56 shows a notch filter (receiver). The controller 21 controls the wave transmitting device 20 in such a manner that duration time of a transmitted ultrasonic wave by the ultrasonic wave converter 10 becomes longer than delay time.

In the third embodiment, an ultrasonic wave is continuously transmitted at a single frequency "f0", and also the ultrasonic wave converter 10 is vibrated at such a frequency sufficiently lower than the single frequency f0. In the third embodiment, since the low frequency vibration of the ultrasonic wave converter 10 is carried out, a Doppler shift occurs in a reflection wave, so that the frequency of this reflection wave is shifted from the frequency of the transmitted ultrasonic wave. Since the frequency of the reflection signal is shifted from the frequency of the transmitted ultrasonic wave, as indicated in FIG. 9, the frequency of the transmitted ultrasonic wave is removed by employing the notch filter 56 in which the transmitted ultrasonic wave signal is used as the reference signal. As a result, the transmitted ultrasonic wave can be separated from the reflection wave.

Figure 10:
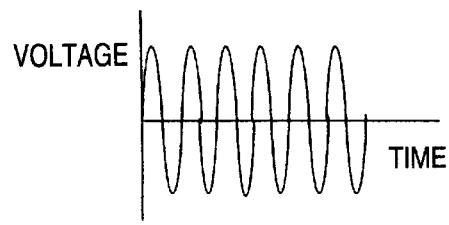
FIG. 10 is a diagram for showing a temporal change of a transmitted ultrasonic wave voltage in the third embodiment of the present invention.
Figure 11:
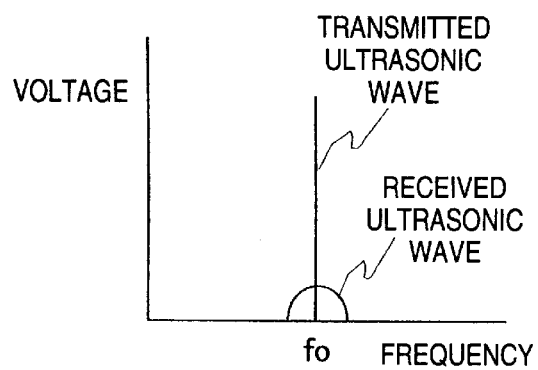
FIG. 11 is a diagram for representing a frequency characteristic of a mixture signal produced by mixing a transmitted ultrasonic wave with a received ultrasonic wave in the third embodiment of the present invention.

FIG. 10 is a diagram for showing a temporal change in transmitted ultrasonic wave voltages of the third embodiment. The frequency of the transmitted ultrasonic wave is a sine wave having a constant frequency (f0). Also, FIG. 11 is a diagram for indicating a frequency characteristic of a mixture signal produced by mixing a transmitted ultrasonic wave with a received ultrasonic wave according to the third embodiment. This drawing shows a condition that a frequency of the received ultrasonic wave is shifted due to a Dapper shift, and this frequency is distributed while centering the frequency "f0" of the transmitted ultrasonic wave.

In the case of a needle-shaped ultrasonic probe, since there is the natural vibration of the needle, this natural vibration may be employed as the low frequency vibration of the ultrasonic wave converter 10. The sound wave may induce the Doppler shift, which is transmitted from the ultrasonic wave converter into the object under examination and then is reflected on the focal point, which the sound wave which is not transmitted into the object under examination, but is reflected in a multiple mode only within the acoustic lens material 2 (which constitutes noise in third embodiment). As a consequence, there is a merit of the method for using the Doppler shift. That is, similar to the ultrasonic wave transmission, the sound wave reflected in the multiple mode (noise) can be removed by the notch filter 56.

Next, the S/N improvement effect according to the present invention will now be simply considered by introducing such an example that the method of the present invention is applied to the needle-shaped ultrasonic probe. For the sake of a simple explanation, all of the transfer time of the detected signals required in the detection, multiplication, A/D conversion, and data acquiring apparatus are neglected, and only the time required for transmitting/receiving the ultrasonic wave signal will be considered. It is now assumed that an image having 100×100=10,000 pixels is acquired by way of the needle-shaped ultrasonic probe within 1 minute to 2 minutes.

In other words, while the needle-shaped ultrasonic probe is mechanically scanned along the x direction and the y direction over 100×100=10,000 points, this needle-shaped ultrasonic probe transmits/receives the ultrasonic waves of the 10,000 points (=100×100) to acquire the signals. Assuming now that one screen is imaged within 100 seconds, the time occupied so as to transmit/receive the ultrasonic waves per 1 point is equal to 10 msec. Even when the conventional method for transmitting the ultrasonic pulse is used, while the scanning operation of the needle-shaped ultrasonic probe is stopped for a predetermined time period, the ultrasonic wave transmission/reception is repeatedly, and the received ultrasonic waves are added to each other, resulting in an improvement of S/N.

However, since the ultrasonic wave transmission is separated from the ultrasonic wave reception in view of a temporal aspect, the next ultrasonic wave cannot be carried out until the ultrasonic wave reception is accomplished. It is now assumed that the delay time "t" is 1 $\mu$sec, the interval between the successive ultrasonic wave transmissions requires on the order of 2 $\mu$sec at minimum, which is twice as 1 $\mu$sec, because the tailing of the received ultrasonic wave occurs, and there is a signal delay caused by the multiple reflection. As a consequence, in accordance with the conventional method, a total wave number of the transmitted/received ultrasonic waves is limited to 5,000 within 10 msec.

On the other hand, in accordance with the present invention, when the frequency of the transmitted ultrasonic wave is equal to, for example, 400 MHz, since the time period is 2.5 nsec, a total wave number of transmittable ultrasonic waves within 10 msec becomes 4,000,000. If the approximation is made by that S/N is direct proportion to a root-menu-square of a total wave number, then an improvement of S/N becomes approximately 30 times ($\sqrt{(4,000,000/5,000)}=\sqrt{(800)}=28.3$), as compared with the limit value of the conventional method. In the conventional method, the adding operations executed 5,000 times are not realistic operation. Normally, a total number of adding operations is on the order of 100 times at maximum. An improvement of S/N becomes 200 times ($\sqrt{(4,000,000/100)}=200$), as compared with a total number of adding operations of 100 times.

In accordance with the present invention, the higher the frequency of the transmitted ultrasonic wave becomes, the larger a total number of ultrasonic waves per unit time becomes. The effect of the improved S/N may be increased.

Figure 12:
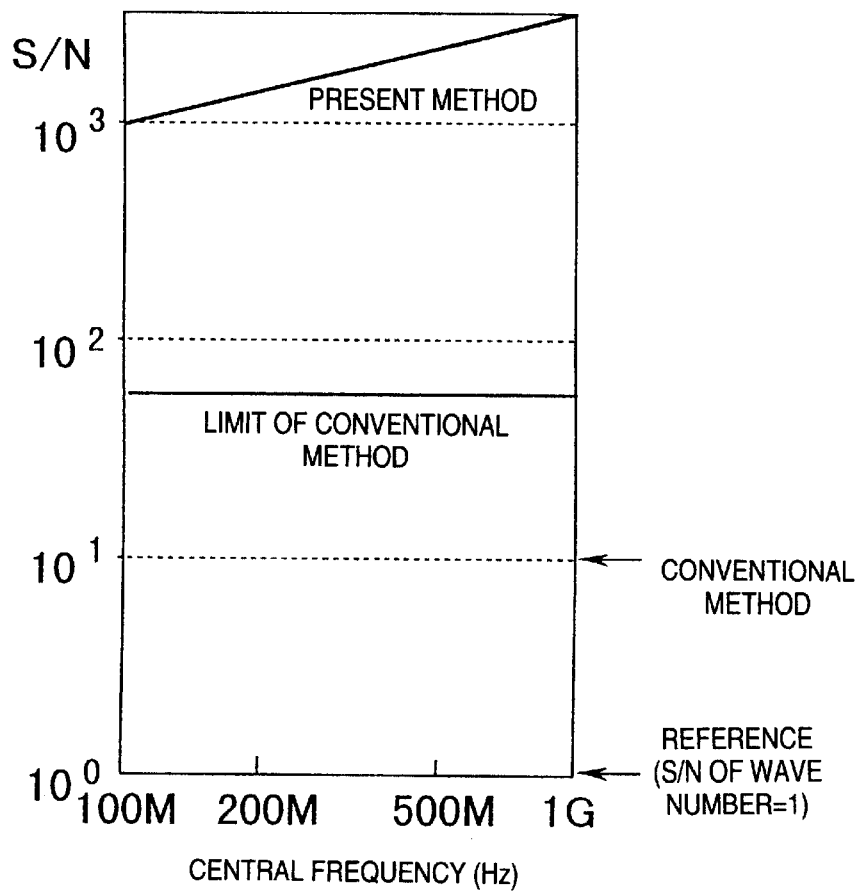
FIG. 12 is a diagram for explaining improved effects of S/N in an ultrasonic imaging method for transmitting a continuous wave in the present invention.

FIG. 12 is a diagram for explaining an effect of improved S/N of the ultrasonic imaging method for transmitting the continuous wave according to the present invention.

In FIG. 12, an abscissa indicates a resonant frequency (central frequency) "f" of an ultrasonic wave converter, and an ordinate shows S/N. In the case that S/N achieved when a total number of transmitted/received ultrasonic waves is equal to 1 is recognized as a reference (S/N=1), this drawing represents S/N in the conventional manner (S/N=10, averaging signals in 100 times), S/N in the limit of the conventional manner (S/N=√5,000=70.7), and also S/N in the present method (method of the present invention). In the conventional method, S/N does not depend upon the frequency of the transmitted ultrasonic wave, whereas in the method of the present invention, S/N is increased in connection with the frequency of the transmitted ultrasonic wave.

As previously explained, in accordance with the present invention, a depth of an imaging plane (namely, distance from acoustic lens) may be determined by a focal distance of an acoustic lens, whereas a thickness of an imaging plane may be determined by a focal depth "d" of an acoustic lens. While using a sound velocity "v", the central frequency "f", and an F value of a lens (namely, a ratio of focal distance to diameter of acoustic lens), the lateral resolution is calculated from $r=F/(v/f)$, and the focal depth is calculated from $d=2 F^2 (v/f)$.

Figure 13:
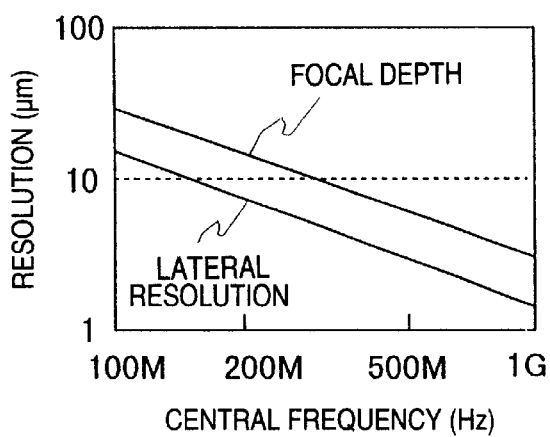
FIG. 13 is a diagram for representing a central frequency depending characteristic of a focal depth and lateral resolution according to the present invention.

FIG. 13 is a diagram for indicating a central frequency depending characteristic between the lateral resolution "r" and the focal depth "d" according to the present invention (assuming now that v=1,500 m/s, F=1).

Apparent from FIG. 13, the lateral resolution "r" is approximately 4 $\mu$m, and the focal depth "d" is 7.5 $\mu$m at the central frequency of 400 MHz. The thickness of the imaging plane defined by the focal depth "d" is relatively thick, but may constitute a practically available value, as compared with a tissue cut piece formed by the living body check method (biopsy). Apparently, when such an acoustic lens having a small F value is employed, a thickness value of an imaging plane can be made small.

(Fourth Embodiment)

Next, a description will now be made of a fourth embodiment realized by that the continuous wave transmitting ultrasonic imaging method according to the present invention is applied to a needle-shaped ultrasonic probe. The present invention is not limited to such an application to the needle-shaped ultrasonic probe, but may be applied a rounded tip-shaped rod type ultrasonic probe, and moreover, applied to another completely different apparatus mode such as an ultrasonic microscope.

Figure 14:
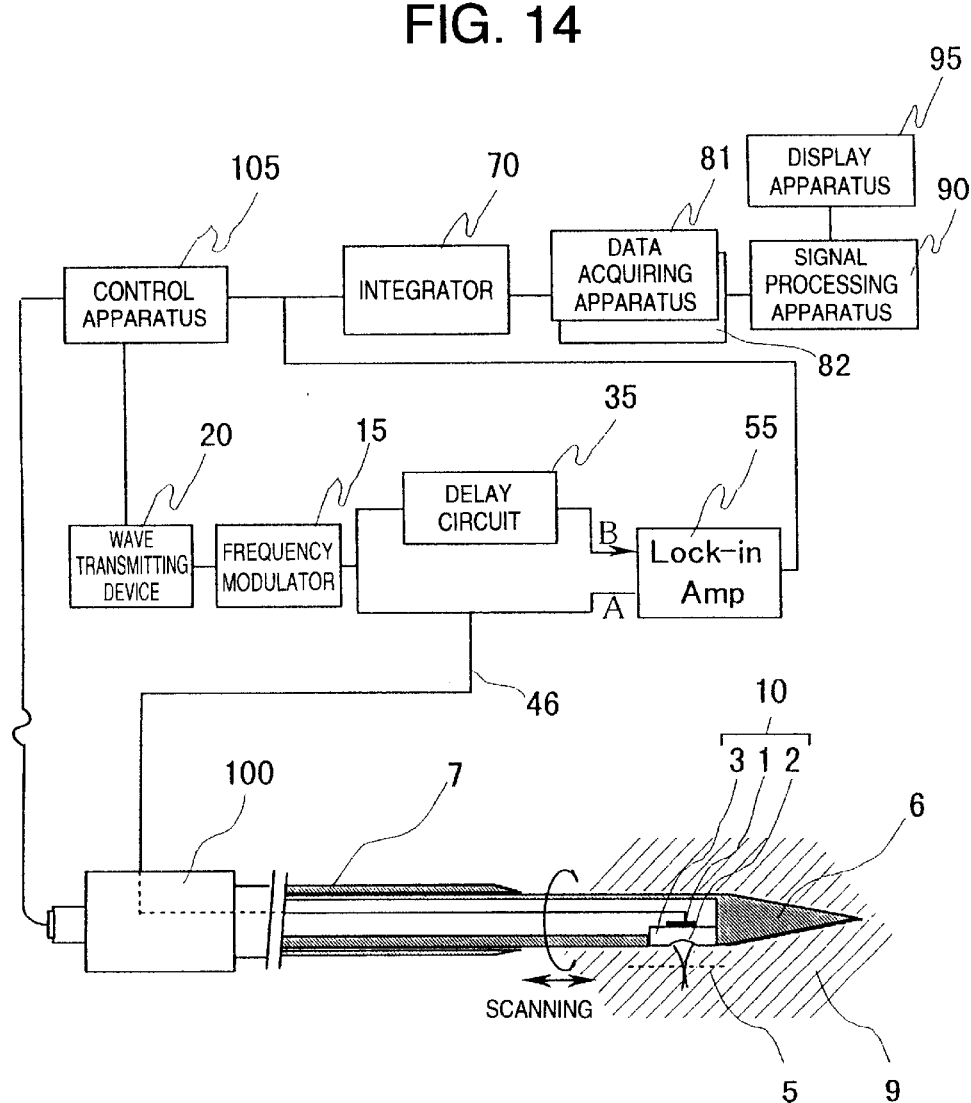
FIG. 14 is a diagram for showing an arrangement of a fourth embodiment in which the ultrasonic imaging method for transmitting the continuous wave, according to the present invention, is applied to a needle type ultrasonic probe.

FIG. 14 is a block diagram for schematically representing an arrangement of the fourth embodiment accomplished by that the continuous wave transmitting ultrasonic imaging method of the present invention is applied to the needle-shaped ultrasonic probe. FIG. 14 is a sectional view for representing such a condition of a needle-shaped ultrasonic probe that an inner needle 6 for mounting the ultrasonic wave converter 10 is exposed from a tip portion of an outer needle 7 within living body tissue 9.

The ultrasonic wave converter 10 is constituted by a piezoelectric transducer element 1 made of zinc oxide (ZnO) sandwiched by gold (Au) electrodes, an acoustic lens material 2 made of sapphire, and an acoustic lens 3 having an F value of 1. The resonant frequency of the piezoelectric transducer element 1 is selected to be, for instance, 400 MHz. The acoustic lens 3 is directly made in contact to the living body tissue 9. The inner needle 6 is moved by a drive apparatus 100, as indicated by an arrow in FIG. 14, along a rotary direction around a shaft of this needle, and also an axial direction. While the needle is moved, the focal point of the acoustic lens 3 draws a cylindrical locus inside the living body tissue 9, and the cylindrical locus corresponds to an imaging plane (curved plane) 5. It should be understood that a control apparatus 105 controls both the mechanical scanning operation of the inner needle 6 of the ultrasonic probe by the drive apparatus 100, and the timing of the transmitted/received ultrasonic wave. The control apparatus 105 controls the wave transmitting device 20 in such a manner that the duration time of the transmitted ultrasonic wave by the ultrasonic wave converter 10 becomes longer than the delay time. Alternatively, either the wave transmitting device 20 or the frequency modulator 15 may be controlled by the controller 21 (not shown).

As an ultrasonic wave transmitting/receiving unit equal to a major unit of the present invention, any one of the arrangements described in the first, second, and third embodiments may be employed. The arrangement indicated in FIG. 14 indicates such a structural example that while an arrangement similar to that of the second embodiment (FIG. 5 and FIG. 6) is employed, a now function is further added. In the arrangement of the second embodiment (FIG. 5 and FIG. 6), considering now that a difference between the frequency f1 and the frequency f2 of the alternating transmitted ultrasonic waves is on the order of 1 MHz, and also there is substantially no difference between the image formed by the frequency f1 and the image formed by the frequency f2, the image is obtained by using the reflection signal derived by the transmitted ultrasonic wave having the frequency f1 and also by the transmitted ultrasonic wave having the frequency f2.

In the example shown in FIG. 14, for example, while the frequency f1 is selected to be 350 MHz and the frequency f2 is selected to be 450 MHz, the difference between the frequencies is intentionally increased, and the image formed from the frequency f1 and the image formed from the frequency f2 are separately stored into a data acquiring apparatus 81 and another data acquiring apparatus 82, respectively. In general, the acoustic characteristics (reflectivity, absorption factor, sound velocity and the like) of the living body tissue 9 are different from each other, depending upon the frequencies. It is conceivable that the differences in the acoustic characteristics caused by the frequency are different from each other every characteristic state of tissue.

As a result, the difference image between the image produced from the frequency f1 and the image produced from the frequency f2 owns such an effect that the distribution of the acoustic characteristic of the living body tissue 9 is emphasized, and also the tissue characteristic shape is made more clearly. In the fourth embodiment, the image processing apparatus 90 may apply a correction to the image data produced by the frequency f1 and the image data produced by the frequency f2, if required, and therefore, can draw the difference image between the image produced by f1 and the image produced by f2. In this correction, the higher the transmission frequency becomes, the smaller the strength of the reception signal becomes. As a consequence, so that the data is converted into such image data produced by any one of these frequencies f1 and f2. The image formed by the frequency f1, the image formed by the frequency f2, and the difference image are displayed on the display apparatus 95. Apparently, the f1-image and the f2-image may be separately displayed, if necessary. Alternatively, an image may be produced by simply adding the f1-image to the f2-image, and then the addition image may be displayed.

In accordance with the fourth embodiment, the depth of the imaging plane (distance from acoustic lens) is determined by the focal distance of the acoustic lens 3, and the thickness of the imaging plane is determined by the focal depth "d" of the acoustic lens. Accordingly, in the fourth embodiment, the imaging plane becomes constant, and a plurality of planes along the depth direction are imaged, so that a three-dimensional image cannot be constituted, which is deteriorated, as compared with the conventional method in which a plurality of imaging planes can be set by the time gate.

Figure 15:
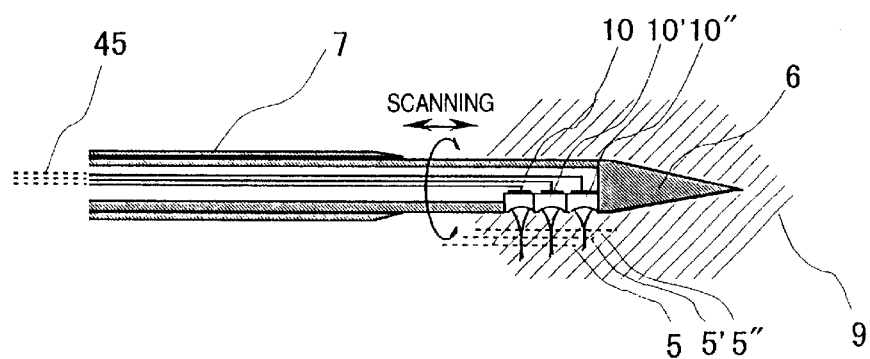
FIG. 15 is a sectional view for indicating another arrangement of the fourth embodiment of the present invention.

FIG. 15 is a sectional view for indicating another arrangement of the fourth embodiment. FIG. 15 represents only a sectional view of a probe for the sake of simplicity. Other arrangements are identical to those of FIG. 14. In accordance with the arrangement shown in FIG. 15, while a plurality of planes along a depth direction are imaged, a three-dimensional image can be arranged. A plurality of ultrasonic wave converters (10, 10', 10") are arranged on a side surface located in the vicinity of a tip portion of an inner needle 6. These ultrasonic wave converters own acoustic lenses having different focal distances from each other. The visual fields which are substantially overlapped with each other are imaged by the respective ultrasonic converters, so that a plurality of imaging planes (5, 5', 5") whose depths are slightly different from each other are obtained. It should be noted that reference numeral 45 shows a bundle of three signal lines used to transmit/receive an ultrasonic wave. Each of the signal lines of the signal line bundle 45 corresponds to a signal line 46 (FIG. 1, FIG. 3, FIG. 9, FIG. 14). The circuits (21, 20, 30, 40, 50 (FIG. 1): 21, 20, 15, 35, 55 (FIG. 3); 21, 20, 56 (FIG. 9); 20, 15, 35, 55 (FIG. 14)) for transmitting/receiving the ultrasonic waves to/from the respective signal lines of the signal line bundle 45 are connected to the respective signal lines.

While a plurality of ultrasonic wave converters are used, it is possible to obtain such a three-dimensional image substantially equivalent to that of the conventional manner. Apparently, when the focal distances of the respective ultrasonic wave converters (10, 10', 10") are made equal to each other, the imaging apparatus may be arranged by which the imaging time of the same imaging plane can be shortened. In the case that a plurality of ultrasonic wave converters are employed, there is a problem about mutual interference among these ultrasonic wave converters. However, in the imaging apparatus according to the present invention, the problem of the mutual interference can be easily solved. In other words, in the conventional imaging method, each of the transmitted/received ultrasonic waves is such a pulse wave having a wide frequency range, and it is practically difficult to prevent the occurrence of such mutual interference while the ultrasonic waves are transmitted/received at the same time.

In accordance with the fourth embodiment, both all of the transmitted ultrasonic waves and all of the received ultrasonic waves of the respective ultrasonic wave converters can be easily set to the frequencies different from each other at an arbitrary time instant.

Figure 16:
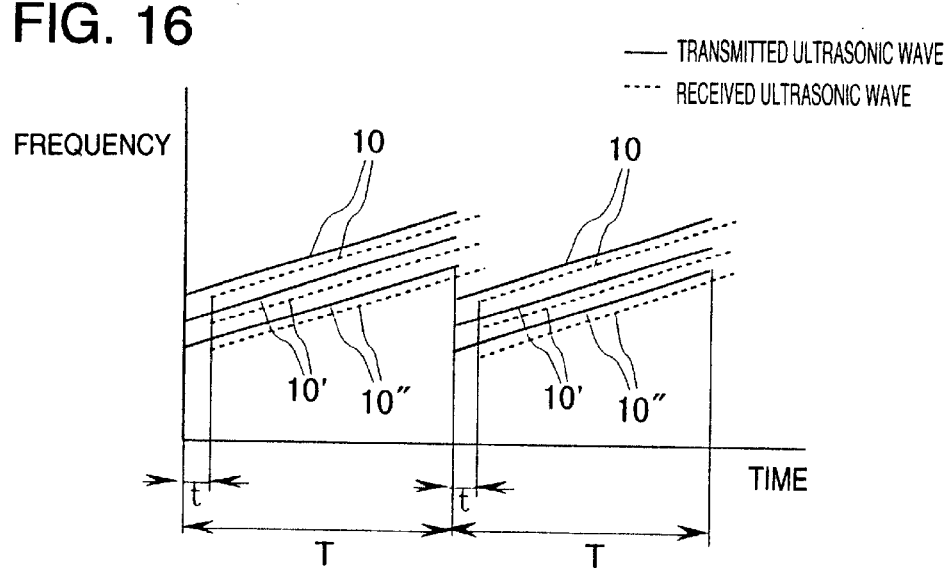
FIG. 16 and FIG. 17 are diagrams for explaining an operation example of a needle-shaped ultrasonic probe according to the fourth embodiment of the present invention.
Figure 17:
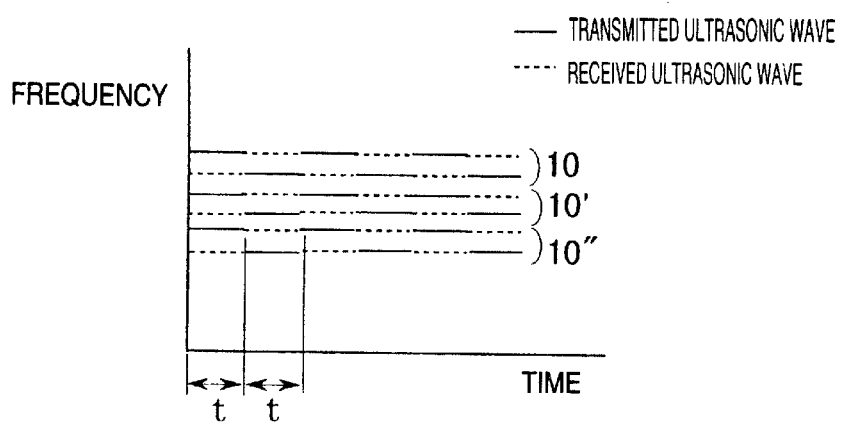

FIG. 16 and FIG. 17 are diagrams for showing methods capable of differing all frequencies of both transmitted ultrasonic waves and received ultrasonic waves from each other in each of the ultrasonic wave converters (10, 10', 10"), namely diagrams for indicating temporal changes in the frequencies of the transmitted/received ultrasonic waves. FIG. 16 is a diagram for showing such an example that a continuous frequency modulation is carried out at different frequencies. FIG. 17 is a diagram for indicating such an example that a frequency modulation is carried out while the respective transmitted ultrasonic waves are alternated among different frequencies. In FIG. 16, while the frequency modulation is repeatedly performed in a time period T, assuming now that this time period "T" is sufficiently longer than the delay time "t", no adverse influence is given to the separation between the transmitted ultrasonic wave and the received ultrasonic wave. In FIG. 16 and FIG. 17, a solid line shows timing of a transmitted ultrasonic wave in each of the ultrasonic wave converters (10, 10', 10"), and a dotted line indicates reception timing. That is, while the delay time "t" is applied to the transmitted ultrasonic wave to produce a reference signal, a mixture signal obtained by mixing a transmitted ultrasonic wave with a received ultrasonic wave is lock-in-detected, so that only a reflection signal is mainly detected. In FIG. 16 and FIG. 17, the temporal change in the frequency of the received ultrasonic wave is identical to the temporal change in the frequency of the reference signal obtained by applying the delay time "t" to the transmitted ultrasonic wave.

(Fifth Embodiment)

Figure 18:
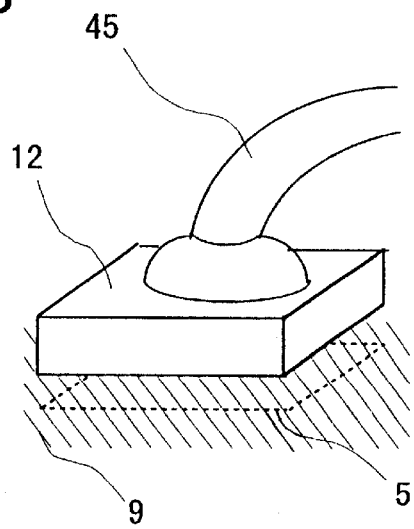
FIG. 18 is a schematic diagram for showing an arrangement of a fifth embodiment in which the present invention is applied to a structure other than the needle-shaped ultrasonic probe.

FIG. 18 is a diagram for schematically showing an arrangement of a fifth embodiment in which the present invention is applied to an arrangement other than the needle-shaped ultrasonic probe, namely such an example that a continuous wave transmitting ultrasonic imaging method is applied to a secondary sensor. In FIG. 18, only a probe is indicated for the sake of simplicity, and other arrangements are identical to those of FIG. 14.

FIG. 18 shows an outer view of the ultrasonic probe. This probe is such an ultrasonic probe that while a sensor unit 12 on which ultrasonic wave converters are mounted in a two-dimensional manner is made in contact with the surface of the living body (biological body) tissue 9, for example, a body surface, an image of a plane (imaging plane 5) under the body surface is obtained. It should be noted that reference numeral 45 shows a bundle of three signal lines used to transmit/receive an ultrasonic wave. Each of the signal lines of the signal line bundle 45 corresponds to a signal line 46 (FIG. 1, FIG. 3, FIG. 9, FIG. 14). The circuits (21, 20, 30, 40, 50 (FIG. 1): 21, 20, 15, 35, 55 (FIG. 3); 21, 20, 56 (FIG. 9); 20, 15, 35, 55 (FIG. 14)) for transmitting/receiving the ultrasonic waves to/from the respective signal lines of the signal line bundle 45 are connected to the respective signal lines.

Figure 19:
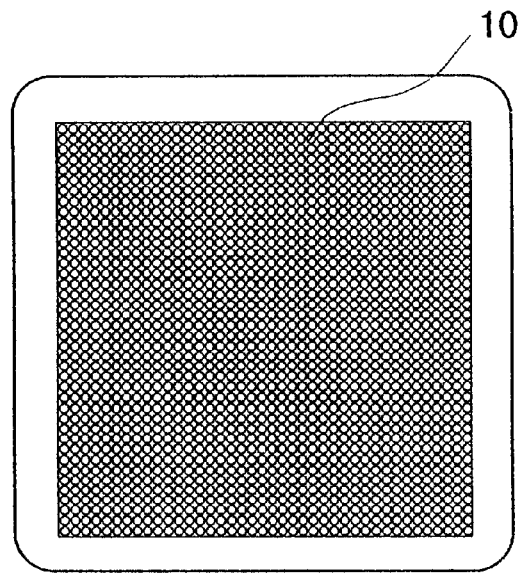
FIG. 19 is a diagram for indicating a lower surface of a sensor unit according to the fifth embodiment of the present invention.

FIG. 19 is a diagram for showing a lower surface of a sensor unit according to the fifth embodiment, namely represents that the acoustic lenses 3 of the ultrasonic wave converters 10 are arranged in a two dimensional manner. In FIG. 19, there is shown such an example that 2,500 (=50× 50) pieces of ultrasonic wave converters 10 each having the acoustic lens 3, the diameter of which is 1 mm, are arranged along two directions perpendicular to each other. The respective acoustic lenses 3 have focal distances of, for example, 2 mm equal to each other, and the imaging plane 5 (FIG. 18) is defined by the focal distances. It is practically difficult to transmit/receive the ultrasonic waves having the different frequencies from each other by all of 2,500 pieces of ultrasonic wave converters shown in FIG. 19.

Figure 20:
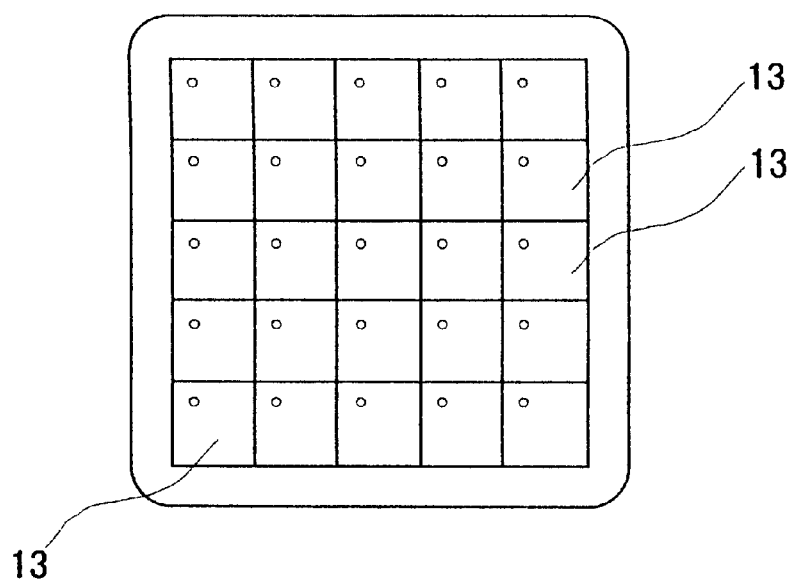
FIG. 20 is a plan view for indicating a structure of an ultrasonic wave converter segmented into a plurality of blocks constructed of a plurality of piezoelectric transducer elements in the fifth embodiment of the present invention.
Figure 21:
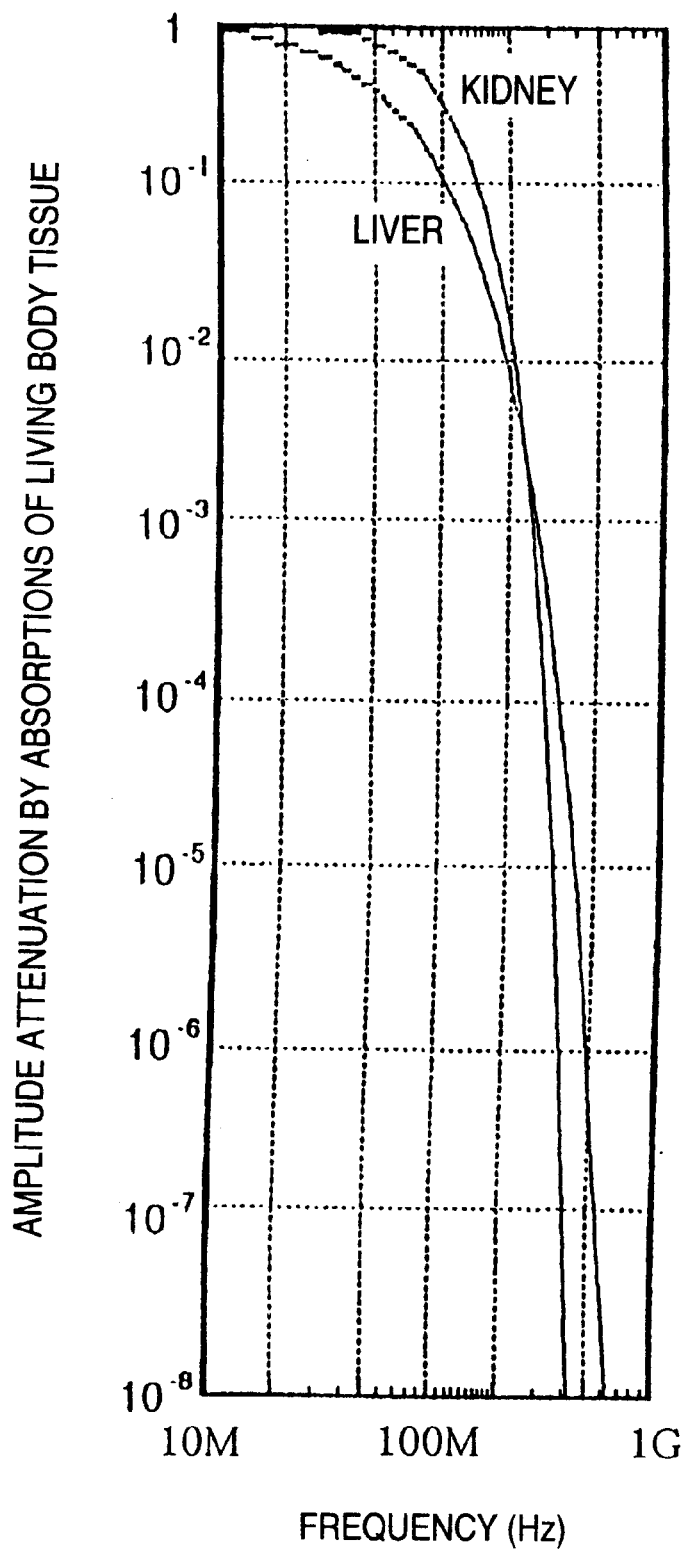
FIG. 21 is a diagram for indicating an attenuation characteristic of an amplitude caused by an absorption of biological body tissue.

FIG. 20 is a plan view for showing a structure of an ultrasonic wave converter which is sequenced into a plurality of blocks made of a plurality of piezoelectric transducer elements, in accordance with the fifth embodiment.

It is practically difficult to transmit/receive the ultrasonic waves at the different frequencies from each other by all of 2,500 pieces of ultrasonic wave converters. Therefore, as indicated in FIG. 20, all of these ultrasonic wave converters are segmented into 25 (=5×5) pieces of blocks 13 constituted by 100 (=10×10) pieces of ultrasonic wave converters. A dimension of each block 13 is defined by 10 mm×10 mm. Assuming now that the used frequency range is selected to be 100 MHz to 200 MHz, in accordance with a method similar to the ultrasonic transmitting/receiving method as explained in FIG. 17, the frequencies different by 500 KHz from each other may be allocated to the ultrasonic wave transmitting/receiving operations executed by 100 pieces of ultrasonic wave converters provided within 1 block.

All of the frequencies allocated to 100 pieces of these ultrasonic wave converters within 1 block are different from each other. When the frequencies are allocated to 100 pieces of ultrasonic wave converters provided within each block, the relationships between the array of 100 pieces of ultrasonic wave converters within each block and the allocations of the frequencies are made equal to each other, in other words, the arrays of the frequencies are made identical to each other, which are allocated to 100 pieces of ultrasonic wave converters employed in each of the blocks, so that the distance between the ultrasonic wave converters which use the same frequency between the adjoining blocks becomes at least 10 mm. In FIG. 20, a circular symbol indicated in each of the blocks 13 represents a position to which the frequency "f0" present in the range between 100 MHz and 200 MHz is allocated. These positions are arranged in an interval of 10 mm identical to one edge of the block. Considering an absorption of the living body tissue 9 and indicating the positions of the ultrasonic wave converters, the mutual interference between a specific ultrasonic wave converter and another ultrasonic wave converter separated from this specific ultrasonic wave converter longer than 10 mm is negligible small, as compared with a signal derived from a focal point of an ultrasonic wave converter which is separated from the specific ultrasonic wave converter by 2 mm. In the fifth embodiment, while the viewing field is 50 mm×50 mm, the number of blocks 13 is increased, so that the viewing field can be enlarged.

In the fifth embodiment, there is such a problem that the lateral resolution is limited by the array density of the ultrasonic wave converters. However, there is such a merit that since the sensor need not be mechanically scanned, the imaging operation can be done within short time.

(Sixth Embodiment)

Next, a description will now be made of an example in which the present invention is applied to a method for measuring a moving state of a humor (fluid) inside of a checking object such as a blood flow. In the case that a checking object approaches to an ultrasonic wave converter in a velocity "v", a relationship between a frequency "F1" of a transmitted ultrasonic wave and a frequency "F2" of a received ultrasonic wave which receives a Dopper shift is given as follows, assuming now that a sound velocity is indicated as "c" and a Dopper shift frequency is expressed as "Df": F2=F1 (1+2 v/c)), and Df=F2−F1. A velocity of a blood flow within a capillary vessel is given as v=1 mm/sec. As a typical value, assuming now that F1=400 MHz and c=1,500 m/sec, Df=530 Hz. In other words, when the frequency of the received ultrasonic wave is made different from the frequency of the transmitted frequency before the delay time "t", it can be understood that there is a fluid having a flow velocity (either blow flow or flow of cell humor) at a focal point position of the transmitted ultrasonic wave.

Figure 22:
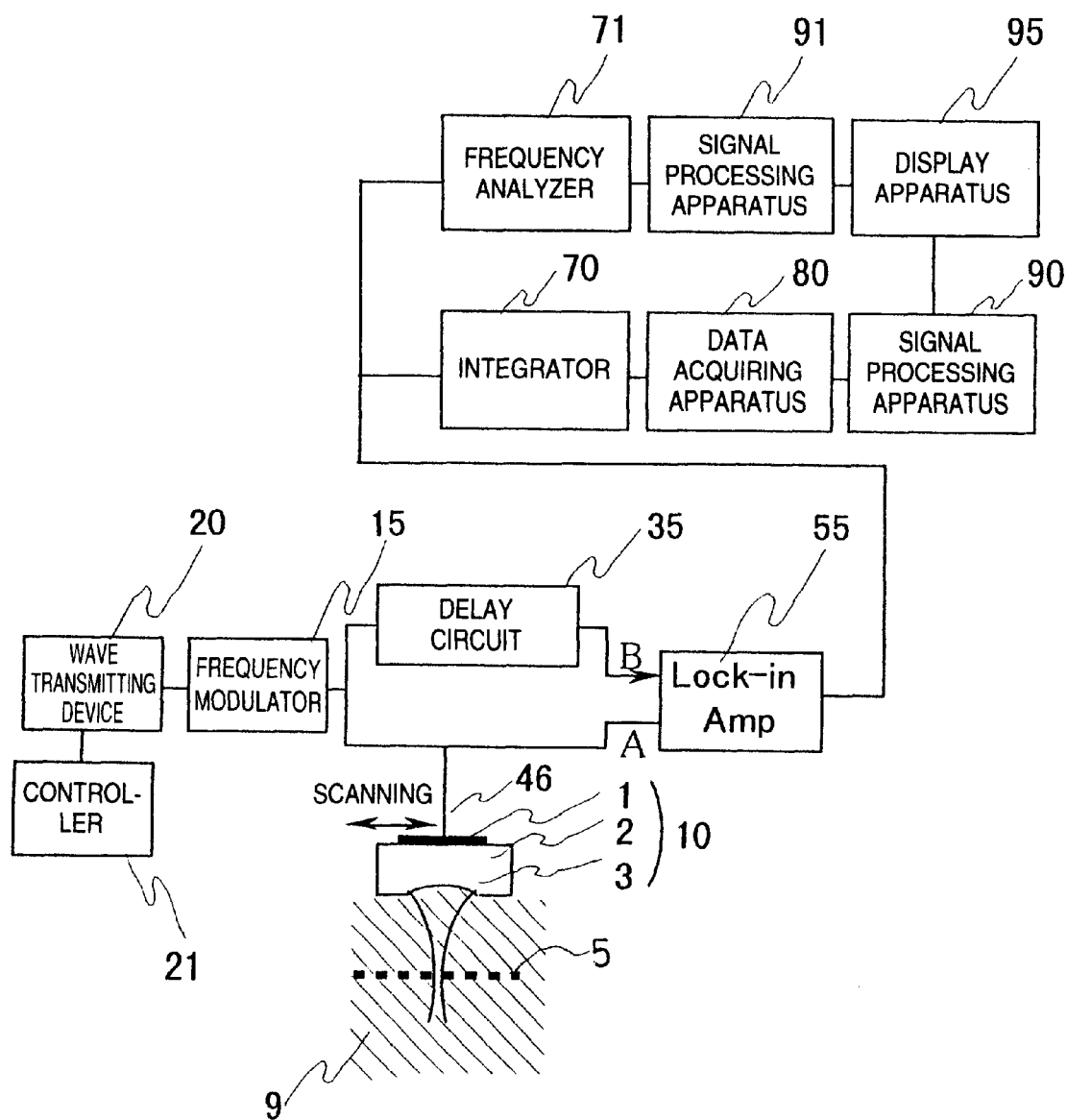
FIG. 22 is a diagram for representing a structural example of an apparatus for measuring moving states of a humor such as a blood flow, according to a sixth embodiment of the present invention.

FIG. 22 is a diagram for indicating a structural example of an apparatus for measuring a moving state of a humor such as a blood flow, according to a sixth embodiment. In FIG. 22, it is assumed that a lock-in-detector (wave receiving device) 55 employed in a wave detection owns a frequency range defined by approximately 2 KHz. After the received ultrasonic wave signal is lock-in-detected to increase S/N of this ultrasonic wave signal, a frequency of this detected ultrasonic wave signal is measured by a high-precision frequency analyzer 71, so that a blood flow velocity (flow rate) at a measurement position can be detected. It should be understood that the arrangement shown in FIG. 22 is formed by adding both the frequency analyzer 71 and a signal processing apparatus 91 to the arrangement of the second embodiment (FIG. 4). Either the wave transmitting device 20 or the frequency modulator 15 is controlled by the controller 21 in such a way that the duration time of the transmitted ultrasonic wave by the ultrasonic wave converter 10 becomes longer than the delay time.

Figure 23:
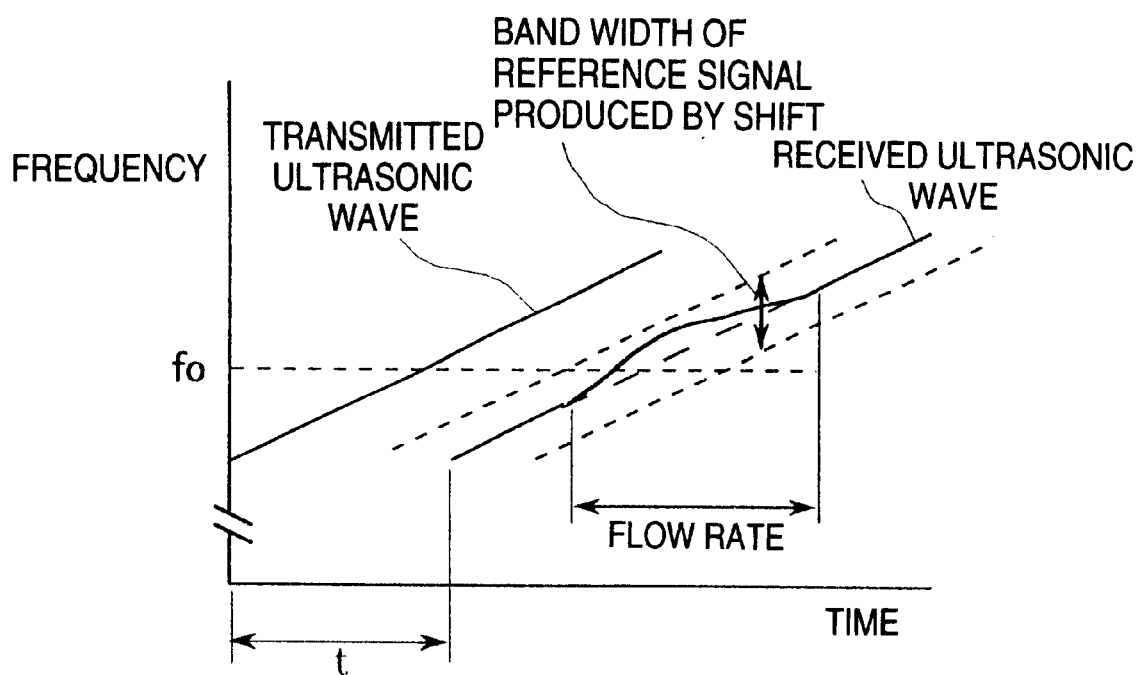
FIG. 23 is a diagram for representing a relationship between a transmitted ultrasonic wave frequency and a received ultrasonic wave frequency, in accordance with the sixth embodiment of the present invention.

FIG. 23 is a drawing for exemplifying a relationship between a frequency of a transmitted ultrasonic wave and a frequency of a received ultrasonic wave in accordance with the method for measuring the moving state of the humor such as the blood flow. In the sixth embodiment, the frequencies between the transmitted ultrasonic wave and the received ultrasonic wave are always made different from each other by approximately 1 MHz, so that there is no problem in the frequency shift of on the order of Df=530 Hz. As a result, in such a case that the ultrasonic wave is received within the range of the reference signal produced by shifting the frequency of the transmitted ultrasonic wave and also the frequency of the received ultrasonic wave is different from the frequency of the transmitted ultrasonic wave before the delay time "t", the presence of the flow velocity (either blood flow or flow of cell fluid) at the focal point position of the transmitted ultrasonic wave is detected. A time range when the flow velocities are detected is indicated in FIG. 23.

The information about the detected flow velocity is converted into perceived color information by the signal processing apparatus 91 different from the signal processing apparatus 90 shown in FIG. 22 by employing the known quasi-coloring method. The converted color information is displayed on the display apparatus 95, while being over-lapped with the image of the acquired imaging plane 5.

In the above-explained description, the transmitted/received ultrasonic waves shown in FIG. 7 of the second embodiment are explained. Even when the present invention is applied to the transmitted/received ultrasonic waves of the second embodiment shown in FIG. 5 and FIG. 8, the moving state of the humor such as the blood flow may be similarly detected.

While the present invention has been described based on the embodiments, the present invention is not limited to these embodiments, but may be modified, changed, or substituted without departing from the technical scope and spirit of the present invention.

The effects achieved by the typical arrangements of the present invention will now be simply explained as follows:

(1). Since the continuous wave is used, a total number of transmitted/received ultrasonic waves is largely increased, and S/N can be improved. For instance, when the S/N is approximated while exemplifying a needle-shaped ultrasonic probe, the resultant effect of this S/N may be increased approximately 30 times higher than the limit value of the conventional method.

(2). Since the frequency range of the received ultrasonic wave can be made narrow, there is such an effect that the temporally delayed signal may be received, and the S/N can be further improved.

(3). Since the ultrasonic having the narrow frequency range is used, no color aberration occurs, so that the lateral resolution can be improved.

(4). A difference in the acoustic characteristics at different frequencies can be easily represented as an image.

(5). Even when a plurality of ultrasonic wave converters are employed so as to acquire a three-dimensional image, the frequencies of the transmitted/received ultrasonic waves of the respective ultrasonic wave converters can be set to different values from each other, and thus, no mutual interference occurs.

Finally, reference numerals employed in the respective drawings will now be summarized. Reference numeral 1 is a piezoelectric transducer element; reference numeral 2 shows an acoustic lens material; reference numeral 3 indicates an acoustic lens; reference numerals 5, 5', 5" represent imaging planes. Also, reference numeral 6 shows an inner needle; reference numeral 7 represents an outer needle; reference numeral 8 is a piezoelectric transducer element having a low resonant frequency; reference numeral 9 is living body tissue (object under examination); reference numeral 10 represents an ultrasonic wave converter; reference numeral 12 shows a sensor unit; reference numeral 13 is a block made of a plurality of piezoelectric transducer elements; reference numeral 15 denotes a frequency modulator. Also, reference numeral 20 shows a wave transmitting device; reference numeral 21 indicates a controller; reference numeral 30 shows an amplitude adjusting device; reference numeral 35 is a delay circuit. Furthermore, reference numeral 40 shows a phase adjusting device; reference numeral 45 indicates a bundle of signal lines; reference numeral 46 shows a signal line; and reference numeral 50 is a differential amplifier. Also, reference numeral 55 is a lock-in-amplifier; reference numeral 56 shows a notch filter; reference numeral 60 represents a detector; reference numeral 70 is an integrator; reference numeral 71 shows a frequency analyzer; reference numerals 80, 81, 82 show data acquiring apparatus; reference numeral denotes a signal processing apparatus; reference numeral represents a signal processing apparatus; reference numeral 95 is a display apparatus; reference numeral 100 shows a drive apparatus, and reference numeral 105 indicates a control apparatus.

What is claimed is:

1. A continuous wave transmission/reception type ultrasonic imaging apparatus comprising: a piezoelectric transducer element (1); an acoustic lens (3) for converging ultrasonic waves; at least one ultrasonic wave converter (10) for transmitting/receiving an ultrasonic wave with respect to a checking object (9); a wave transmitting device (20) for supplying a transmitted ultrasonic wave signal to said ultrasonic wave converter; a wave receiving device (50, 55, 56) for receiving an ultrasonic wave reflected from said checking object; a scanning mechanism for scanning said ultrasonic wave converter on either a plain surface or a curved surface perpendicular to a propagation direction of the ultrasonic wave transmitted/received by said ultrasonic wave converter; and a controller (21, 105) for controlling duration time of the transmitted ultrasonic wave by said ultrasonic wave converter to become longer than delay time corresponding to a time difference between a time instant when said piezoelectric transducer element is energized by said transmitted ultrasonic wave signal and another time instant when an ultrasonic wave produced by being energized is propagated to a focal distance of said acoustic lens to be reflected, and is again propagated to said piezoelectric transducer element so as to be converted into a voltage.

2. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is periodically alternated between at least two sets of discontinues frequencies different from each other; when symbol "n" is recognized as a natural number, an alternating time period of a frequency of the sine wave is equal to be $2/(2n-1)$ times longer than said delay time; and said ultrasonic wave receiver receives said reflected ultrasonic wave with reference to said transmitted ultrasonic wave signal.

3. A continuous wave transmission/reception type ultrasonic imaging apparatus as claimed in claim 2 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means.

4. A continuous wave transmission/reception type ultrasonic imaging apparatus as claimed in claim 2 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means; and means (90) for constituting a difference image between images obtained by said different transmitted ultrasonic frequencies by using image data which are obtained by employing the received ultrasonic wave signals acquired every said discontinuous transmitted ultrasonic wave frequencies different from each other.

5. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is periodically alternated between two sets of discontinuous frequencies different from each other; when symbol "n" is recognized as a natural number, an alternating time period of a frequency of the sine wave is equal to be $2/(2n-1)$ times longer than said delay time; and said ultrasonic wave receiver receives said reflected ultrasonic wave with reference to said transmitted ultrasonic wave signal which is delayed by either time $(2n-1)/2$ times longer than said alternating time period, or time equal to said delay time.

6. A continuous wave transmission/reception type ultrasonic imaging apparatus as claimed in claim 5 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means.

7. A continuous wave transmission/reception type ultrasonic imaging apparatus as claimed in claim 5 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means; and means (90) for constituting a difference image between images obtained by said different transmitted ultrasonic wave frequencies by using image data which are obtained by employing the received ultrasonic wave signals acquired every said discontinuous transmitted ultrasonic wave frequencies different from each other.

8. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is continuously and periodically changed; when symbol "n" is recognized as a natural number, a changing time period of a frequency of the sine wave is equal to be $2/(2n-1)$ times longer than said delay time; and said ultrasonic wave receiver receives said reflected ultrasonic wave with reference to said transmitted ultrasonic wave signal.

9. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is continuously and periodically changed; when symbol "n" is recognized as a natural number, a changing time period of a frequency of the sine wave is equal to be $2/(2n-1)$ times longer than said delay time; and said ultrasonic wave receiver receives said reflected ultrasonic wave with reference to said transmitted ultrasonic wave signal which is delayed by either time $(2n-1)/2$ times longer than said alternating time period, or time equal to said delay time.

10. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is continuously changed; and said ultrasonic wave receiver receives said reflected ultrasonic wave with reference to said transmitted ultrasonic wave signal which is delayed by time equal to said delay time.

11. A continuous wave transmission/reception type ultrasonic imaging apparatus as claimed in claim 1 wherein:

the ultrasonic wave transmitted by the ultrasonic wave converter is a sine wave produced by that a frequency of the transmitted ultrasonic wave is changed in a discontinuous manner every time a constant time period has passed; time during which a constant frequency is continued is shorten than said delay time; and said wave receiving device receives the reflected ultrasonic wave with reference to said transmitted ultrasonic wave signal delayed by time equal to said delay time.

12. A continuous wave transmission/reception type ultrasonic imaging apparatus as claimed in claim 11 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means.

13. A continuous wave transmission/reception type ultrasonic imaging apparatus as claimed in claim 11 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means; and means (90) for constituting a difference image between images obtained by said different transmitted ultrasonic wave frequencies by using image data which are obtained by employing the received ultrasonic wave signals acquired every said discontinuous transmitted ultrasonic wave frequencies different from each other.

14. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is changed in a discontinuous manner; time during which a constant frequency is continued is always shorter than said delay time; and said ultrasonic wave receiver receives said reflected ultrasonic wave with reference to said transmitted ultrasonic wave signal which is delayed by time equal to said delay time.

15. A continuous wave transmission/reception type ultrasonic imaging apparatus as claimed in claim 14 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means.

16. A continuous wave transmission/reception type ultrasonic imaging apparatus as claimed in claim 14 wherein:

said imaging apparatus includes signal acquiring means (81, 82), the number of which is equal to a total number of said different frequencies of the transmitted ultrasonic waves, so that the received ultrasonic wave signals obtained with respect to each of the different transmitted ultrasonic frequencies are acquired by another signal acquiring means; and means (90) for constituting a difference image between images obtained by said different transmitted ultrasonic wave frequencies by using image data which are obtained by employing the received ultrasonic wave signals acquired every said discontinuous transmitted ultrasonic wave frequencies different from each other.

17. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is constant; said ultrasonic wave converter includes a mechanism operated along a direction parallel to a propagation direction of the ultrasonic wave transmitted/received by said ultrasonic wave converter; and said wave receiving device receives said reflected ultrasonic wave with reference to said transmitted ultrasonic wave signal.

18. A continuous wave transmission/reception type ultrasonic imaging apparatus as claimed in claim 1 wherein:

the ultrasonic wave transmitted by said ultrasonic wave converter is a sine wave produced by that a frequency of a transmitted ultrasonic wave is constant; and said wave receiving device detects a difference between a reference signal and the output signal of said ultrasonic wave converter, said reference signal being produced by adjusting an amplitude and a phase of said transmitted ultrasonic wave signal.

19. A continuous wave transmission/reception type ultrasonic imaging apparatus as claimed in claim 1 wherein:

said imaging apparatus includes a sensor unit (12) on which said ultrasonic wave converter is mounted in a two-dimensional manner.

20. A continuous wave transmission/reception type ultrasonic imaging apparatus as claimed in claim 1 wherein:

said imaging apparatus includes a sensor unit (12) on which said ultrasonic wave converter is mounted in a two-dimensional manner; said sensor unit is subdivided into a plurality of blocks (13) constituted by a preselected plural number of ultrasonic wave converters; and the frequencies of the transmitted/received ultrasonic waves of each of said ultrasonic wave converters within each of said plural blocks are made different from each other.

21. A continuous wave transmission/reception type ultrasonic imaging apparatus as claimed in claim 1 wherein:

said imaging apparatus includes means (55, 71, 91) for detecting a flow velocity of a fluid within said checking object from the ultrasonic wave signal received by said wave receiving device.

22. A needle-shaped, or rod-shaped continuous wave transmission/reception type ultrasonic probe employed in the continuous wave transmission/reception type ultrasonic wave imaging apparatus as recited in claim 1 of the scope of claim, wherein:

a shape of said continuous wave transmission/reception type ultrasonic wave probe is made of either a rod shape or a piercing-needle shape (6); a propergation direction of an ultrasonic wave transmitted/received by said ultrasonic wave converter is equal to a direction perpendicular to an axis of said continuous wave transmission/reception ultrasonic probe; and said ultrasonic wave converter is scanned along the axial direction, or a rotation direction around said axis by said scanning mechanism under such a condition that said continuous wave transmission/reception type ultrasonic probe is made in close contact with a surface of a living body (biological body), is inserted into said living body, or is pierced into said living body; whereby said ultrasonic probe measures living body tissue on a cylindrical plane around an axis formed by a locus of a focal point of said acoustic lens.

23. A continuous wave transmission/reception type ultrasonic probe as claimed in claim 22 wherein:

the frequencies of the transmitted/received ultrasonic waves of said respective ultrasonic wave converters are different from each other.

24. A continuous wave transmission/reception type ultrasonic probe as claimed in claim 23 wherein:

said ultrasonic probe contains a plurality of said ultrasonic wave converters; the acoustic lenses of the respective ultrasonic wave converters own focal distances different from each other; and a viewing field in the axial direction along which each of said ultrasonic wave converters is scanned is overlapped with a viewing field in the rotation direction around the axis.

25. A continuous wave transmission/reception type ultrasonic imaging apparatus comprising: a piezoelectric transducer element (1); an acoustic lens (3) for converging ultrasonic waves; an ultrasonic wave converter (10) for transmitting/receiving an ultrasonic wave with respect to a checking object (9); a wave transmitting device (20) for supplying a transmitted ultrasonic wave signal to said ultrasonic wave converter; a wave receiving device (50, 55, 56) for receiving an ultrasonic wave reflected from said checking object; means for scanning said ultrasonic wave converter in a predetermined direction; and a controller (21, 105) for maintaining duration time of the transmitted ultrasonic wave by said ultrasonic wave converter longer than a time difference between a time instant when said piezoelectric transducer element is energized by said transmitted ultrasonic wave signal and another time instant when an ultrasonic wave produced by being energized is propagated to a focal distance of said acoustic lens to be reflected, and is again propagated to said piezoelectric transducer element so as to be converted into a voltage.

26. A continuous wave transmission/reception type ultrasonic imaging apparatus as claimed in claim 25 wherein:

the ultrasonic wave transmitted by said ultrasonic wave converter is a sine wave produced by that a frequency of a transmitted ultrasonic wave is periodically alternated between two sets of discontinuous frequencies different from each other; an alternating time period of a frequency of the sine wave is equal to be 2 times longer than said time difference; and said ultrasonic wave receiver receives said reflected ultrasonic wave with reference to said transmitted ultrasonic wave signal which is delayed by either time ½ times longer than said alternating time period, or time equal to said time difference.

* * * * *